United States Patent
Yersin et al.

(10) Patent No.: US 9,543,531 B2
(45) Date of Patent: Jan. 10, 2017

(54) ORGANIC ELECTROLUMINESCENT DEVICE

(75) Inventors: Hartmut Yersin, Sinzing (DE); Uwe Monkowius, Linz (AT); Tobias Fischer, Rimbach (DE)

(73) Assignee: Merck Patent GmbH, Darmstadt (DE)

( * ) Notice: Subject to any disclaimer, the term of this patent is extended or adjusted under 35 U.S.C. 154(b) by 789 days.

(21) Appl. No.: 13/001,664

(22) PCT Filed: Sep. 25, 2009

(86) PCT No.: PCT/EP2009/006940
§ 371 (c)(1),
(2), (4) Date: Jul. 22, 2011

(87) PCT Pub. No.: WO2010/046016
PCT Pub. Date: Apr. 29, 2010

(65) Prior Publication Data
US 2011/0275818 A1    Nov. 10, 2011

(30) Foreign Application Priority Data

Oct. 24, 2008 (DE) ........................ 10 2008 053 121

(51) Int. Cl.
| | | |
|---|---|---|
| H01L 51/54 | (2006.01) | |
| C09K 11/06 | (2006.01) | |
| H01L 51/00 | (2006.01) | |
| C07F 15/00 | (2006.01) | |
| H01L 51/50 | (2006.01) | |

(52) U.S. Cl.
CPC ....... H01L 51/0085 (2013.01); C07F 15/0086 (2013.01); C07F 15/0093 (2013.01); C09K 11/06 (2013.01); H01L 51/0084 (2013.01); H01L 51/0087 (2013.01); C09K 2211/1029 (2013.01); C09K 2211/185 (2013.01); H01L 51/0042 (2013.01); H01L 51/5016 (2013.01); H01L 2251/5384 (2013.01)

(58) Field of Classification Search
CPC .... H01L 51/005; H01L 51/0087; H01L 51/50; H01L 51/5012; H01L 51/5016; H01L 51/5032; C09K 11/06; C09K 2211/185
See application file for complete search history.

(56) References Cited

U.S. PATENT DOCUMENTS

| | | | | |
|---|---|---|---|---|
| 2001/0030508 A1* | 10/2001 | Utsugi et al. | ................. | 313/505 |
| 2002/0042174 A1* | 4/2002 | Kunugi et al. | ................. | 438/199 |
| 2007/0111025 A1* | 5/2007 | Lennartz et al. | ............. | 428/690 |
| 2008/0036368 A1 | 2/2008 | Frampton et al. | | |
| 2009/0206735 A1 | 8/2009 | Yersin et al. | | |
| 2010/0059740 A1 | 3/2010 | Yersin et al. | | |
| 2011/0177630 A1* | 7/2011 | De Cola et al. | ................. | 438/22 |
| 2012/0313087 A1 | 12/2012 | Buchholz et al. | | |
| 2013/0020560 A1 | 1/2013 | Yersin et al. | | |

FOREIGN PATENT DOCUMENTS

| | | | |
|---|---|---|---|
| EP | 0277032 A2 | 8/1988 | |
| WO | WO-2007/118671 A1 | 10/2007 | |
| WO | WO-2008/087031 A1 | 7/2008 | |
| WO | WO 2010/037667 A1 * | 4/2010 | ............. C07F 15/00 |

OTHER PUBLICATIONS

Miskowski et al. "Electronic spectra and photophysics of platinum(II) complexes with α—diimine ligands. Solid-state effects. 2. Metal-metal interactions in double salts and linear chains." Inorg. Chem. vol. 30, pp. 4446-4452, 1991.*

Buss, Carrie E., et al. "Synthesis and Characterization of Pt(CN-p-$(C_2H_6)C_6H_4)_2(CN)_2$, a Crystalline Vapoluminescent Compound That Detects Vapor-Phase Aromatic Hydrocarbons", JACS, vol. 124, No. 6, pp. 1031-1039 (2002).

* cited by examiner

Primary Examiner — Marie R. Yamnitzky

(74) Attorney, Agent, or Firm — Drinker Biddle & Reath LLP

(57) ABSTRACT

The present invention relates to the use of double-complex salts in electronic devices, in particular in organic electroluminescent devices, and oligomers formed from charged metal complexes.

3 Claims, 3 Drawing Sheets

Diagrammatic and simplified representation of the way in which an OLED works. The layers applied have, for example, a thickness of about 300 nm.

Excitation and emission spectrum of [Pt(4,4'-dinonyl-2,2'-dipyridyl)$_2$]-[Pt(CN)$_4$] (T = 300 K, $\lambda_{exc.}$ = 365 nm, $\lambda_{det.}$ = 563 nm).

Figure 3

| 7 | Cathode, Al: 60 nm |
|---|---|
| 6 | Interlayer CsF: 0.8 nm |
| 5 | ETL, Alq$_3$: 40 nm |
| 4 | Emitter layer: 30 to 100 nm |
| 3 | HTL, PEDOT: PSS: 50 nm |
| 2 | Anode, ITO: 40 nm |
| 1 | Support material, glass |

Example of an OLED device in which the emitter layer according to the invention is applied by wet-chemical methods. The layer-thickness data are illustrative values.

ORGANIC ELECTROLUMINESCENT DEVICE

RELATED APPLICATIONS

This application is a national stage application (under 35 U.S.C. §371) of PCT/EP2009/006940, filed Sep. 25, 2009, which claims benefit of German Application No. 10 2008 053 121.9, filed Oct. 24, 2008.

The present invention relates to double-complex salts in opto-electronic components and in particular oligomers formed from charged metal complexes for use in OLEDs.

A drastic change is currently evident in the area of display screen and lighting technology. It will be possible to manufacture flat displays or lighting areas with a thickness of less than 0.5 mm. These are distinguished by many fascinating properties. Thus, for example, it is possible to develop lighting areas as wallpapers having very low energy consumption. However, it is particularly interesting that it is possible to produce colour display screens having hitherto unachievable colour fidelity, brightness and viewing-angle independence, having low weight and very low power consumption. It is possible to design the display screens as microdisplays or large display screens having an area of several $m^2$ in rigid or flexible form, but also as transmission or reflection displays. It is furthermore possible to employ simple and cost-saving production processes, such as screen printing, ink-jet printing or vacuum sublimation. This will facilitate very inexpensive manufacture compared with conventional flat display screens. This novel technology is based on the principle of OLEDs, Organic Light Emitting Devices.

Components of this type consist predominantly of organic layers, as shown diagrammatically and in a simplified manner in FIG. 1. At a voltage of, for example, 5 to 10 V, negative electrons exit from a conducting metal layer, for example an aluminium cathode, into a thin electron-conduction layer and migrate in the direction of the positive anode. The latter consists, for example, of a transparent, but electrically conductive, thin indium tin oxide (ITO) layer, from which positive charge carriers, so-called holes, migrate into an organic hole-conduction layer. These holes move in the opposite direction compared with the electrons, more precisely towards the negative cathode. A central layer, the emitter layer, which likewise consists of an organic or organometallic material, additionally contains special emitter molecules, at which or in the vicinity of which the two charge carriers recombine and result in energetically excited states of the emitter molecules.

The excited states then release their energy as light emission, for example in a blue, green or red colour. It may also be possible to omit the emitter layer if the emitter molecules are located in the hole- or electron-conduction layer.

The OLED components can have a large-area design as illumination elements or an extremely small design as pixels for displays. The crucial factor for the construction of highly efficient OLEDs is the light-emitting materials used (emitter molecules). These can be achieved in various ways, using purely organic or organometallic molecules and complex compounds. It can be shown that the light yield of the OLEDs can be significantly greater with organometallic substances, so-called triplet emitters, than for purely organic materials. Owing to this property, the further development of organometallic materials is of essential importance. The function of OLEDs has already been described very frequently (C. Adachi, M. A. Baldo, S. R. Forrest, S. Lamansky, M. E. Thompson, R. C. Kwong, Appl. Phys. Lett. 2001, 78, 1622; X. Yang, D. C. Muller, D. Neher, K. Meerholz, Adv. Mater. 2006, 18, 948; J. Shinar (Ed.), Organic light-emitting devices—A survey, AIP Press, Springer, New York, 2004; H. Yersin, Top. Curr. Chem. 2004, 241, 1; H. Yersin (Ed.), Highly Efficient OLEDs with Phosphorescent Materials, Wiley-VCH, Weinheim 2008; Z. H. Kafafi, Organic Electroluminescence, Taylor & Francis, Boca Raton, 2005). A particularly high efficiency of the device can be achieved using organometallic complexes ("organotransition metal" complexes are frequently abbreviated to "organometallic" complexes) having a high emission quantum yield (from the lowest triplet states to the singlet ground states). These materials are frequently referred to as triplet emitters or phosphorescent emitters. This discovery has been known for some time (C. Adachi, M. A. Baldo, S. R. Forrest, S. Lamansky, M. E. Thompson, R. C. Kwong, Appl. Phys. Lett. 2001, 78, 1622; X. Yang, D. C. Muller, D. Neher, K. Meerholz, Adv. Mater. 2006, 18, 948; J. Shinar (Ed.), Organic light-emitting devices—A survey, AIP Press, Springer, New York, 2004; H. Yersin, Top. Curr. Chem. 2004, 241, 1; H. Yersin (Ed.), Highly Efficient OLEDs with Phosphorescent Materials, Wiley-VCH, Weinheim 2008). Many protective rights have already been applied for or granted for triplet emitters, see, for example: M. E. Thompson, P. I. Djurovich, J. Li (University of Southern California, Los Angeles, Calif.), WO 2004/017043 A2, 2004; M. E. Thompson, P. I. Djurovich, R. Kwong (University of Southern California, Los Angeles, Calif., Universal Display Corp, Ewing, NY), WO 2004/016711 A1, 2004; A. Tsuboyama, S. Okada, T. Takiguchi, K. Ueno, S. Igawa, J. Kamatani, M. Furugori, H. Iwawaki (Canon KK, Tokyo), WO 03/095587 A1, 2003; C.-M. Che, US 2003/0205707 A1, 2003; C.-M. Che, W. Lu, M. C.-W. Chan, US 2002/0179885 A1, 2002; J. Kamatani, S. Okada, A. Tsuboyama, T. Takiguchi, S. Igawa, US 2003/186080 A1, 2003; P. Stößel, I. Bach, A. Büsing (Covion Organic Semiconductors GmbH), DE 10350606 A1, 2005; M. Bold, C. Lennartz, M. Egen, H.-W. Schmidt, M. Thelakkat, M. Bäte, C. Neuber, W. Kowalsky, C. Schildknecht (BASF AG), DE 10338550 A1, 2005; C. Lennartz, A. Vogler, V. Pawlowski (BASF AG), DE 10358665 A1, 2005; B. Hsieh, T. P. S. Thoms, J. P. Chen (Canon KK, Tokyo), US 2006/989273 B2, 2006; N. Schulte, S. Heun, I. Bach, P. Stoessel, K. Treacher (Covion Organic Semiconductors), WO 2006/003000 A1, 2006; A. Vogler, V. Pawlowski, H.-W. Schmidt, M. Thelakkat (BASF AG), WO 2006/032449 A1, 2006; T. K. Hatwar, J. P. Spindler, R. H. Young (Eastman Kodak Co), WO 2006/028546 A1, 2006.

However, there is still a need for improvement in the case of the triplet emitters known to date, in particular in the area of the long-term stability of the emitters in OLED devices with respect to the thermal stability, with respect to the chemical stability to water and oxygen, with respect to the chemical variability, with respect to the availability of important emission colours in suitable colour purity, with respect to manufacturing reproducibility, with respect to suitable energies for the HOMOs and LUMOs, which are important for hole or electron capture, with respect to the achievability of high efficiency at high current densities and/or with respect to the achievability of very high luminous densities.

BRIEF DESCRIPTION OF THE DRAWINGS

FIG. 3 shows an example of an OLED device in which the emitter layer according to the invention is applied by wet-chemical methods.

DETAILED DESCRIPTION OF THE INVENTION

Figure 1:
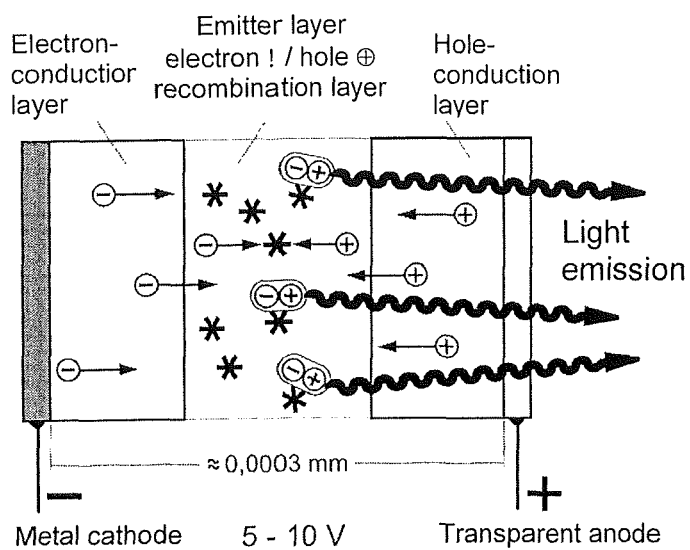
FIG. 1 shows a diagrammatic and simplified representation of the way in which an OLED works.

The invention for use in OLEDs therefore relates to an oligomer comprising at least one positively charged metal complex and at least one negatively charged metal complex, where the metal complexes have the $$K_1 = [L1L2L3L4M1]^{n+} \text{ and} \quad \text{formula (I):}$$

the formula (II):

$$K_2 = [L5L6L7L8M2]^{n-},$$

where M1 and M2 each represent, independently, a metal centre selected from Ir(I), Rh(I), Pt(II), Pd(II), Au(III), and L1, L2, L3 and L4 as well as L5, L6, L7 and L8 each represent, identically or differently on each occurrence, a neutral or charged ligand, where two or more of ligands L1, L2, L3 and L4, and L5, L6, L7 and L8 may also be linked to one another, and n=1 or 2. Ligands L1 to L8 here must be selected so that the overall charge of the complex (n+ or n−), which is indicated and necessary in each case, is retained.

It is also possible here for the oligomer to comprise more than one positively charged complex, for example at least two different positively charged complexes, and more than one negatively charged complex, for example at least two different negatively charged complexes.

The above-mentioned oligomers are employed in electronic devices. An electronic device here is taken to mean a device which comprises at least one layer which comprises at least one organic or organometallic compound or at least one coordination compound containing organic ligands. However, the component may also comprise inorganic materials or layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), but preferably organic electroluminescent devices (OLEDs), particularly preferably phosphorescent OLEDs.

The organic electroluminescent device comprises a cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013).

The common structural feature of all complexes used in the double-complex salts consists in that the central ions M have square-planar or approximately square-planar tetracoordination, where the coordinations may be symmetrical or asymmetrical, asymmetrical arrangements being preferred.

This invention relates to the use of a class of substances in which intense emission (high emission quantum yield) can only arise through a pronounced metal-metal interaction between square-planar, oppositely charged metal complexes. The transitions which result in emission are thus based in this class of compounds on metal-metal interactions of the individual complexes in the oligomer. This represents a major difference from systems to date, in which the light emission is based on isolated, neutral molecules.

Oppositely charged Pt(II) complexes with square-planar or approximately square-planar coordination and structurally related complexes from the second and third periods of the transition metals having a $d^8$ electron configuration (Pd(II), Ir(I), Rh(I) and to a limited extent Au(III)) exhibit a tendency towards the formation of metal-metal interactions and form trimers, tetramers, etc., or oligomers or columnar structures in general (the terms columnar structures, stack arrangement, oligomers and aggregates are used synonymously here). Compounds of this type exhibit, as solids, intense emissions, which possibly result from states which only arise from the metal-metal interactions.

The invention is based on the use of differently charged metal complexes, i.e. double-complex salts which form trimers, tetramers, etc., or oligomers in general, in optoelectronic components which are hermetically screened from the outside. The permeability of the casing for water vapour is preferably $<10^{-6}$ g*m$^{-2}$*d$^{-1}$ and for oxygen is preferably $<10^{-6}$ cm$^3$*m$^{-2}$*d$^{-1}$, bar$^{-1}$, so that there is no gas exchange with the environment.

The term oligomer generally encompasses units having at least 3, preferably at least 4, more preferably at least 5, in particular at least 10 and especially up to 100, preferably up to 50, metal complexes. For the purposes of the present invention, all compounds which comprise at least one metal complex of the formula (I) and at least one metal complex of the formula (II) are regarded as oligomers.

The oligomers to be employed in accordance with the invention are formed from metal complexes of the $$K_1 = [L1L2L3L4M1]^{n+} \text{ and} \quad \text{formula (1):}$$

of the formula (II):

$$K_2 = [L5L6L7L8M2]^{n-}$$

(n=1, 2).

The metal centres M1 and M2 of the metal complexes are selected, independently, from Ir(I), Rh(I), Pt(II), Pd(II) or Au(III), preferably from Pt(II) and Pd(II).

In accordance with the invention, M1=M2 or M1≠M2 is possible. Any desired combinations are also possible, where the charges of the individual complex units must add up to zero in total. Preference is given to oligomers which comprise metal complexes with at least two different metal centres, i.e., in particular, oligomers in which M1≠M2.

L1, L2, L3 and L4, and L5, L6, L7 and L8 each stand, independently, for a neutral or charged ligand, in particular for a monodentate or polydentate ligand. In the following descriptions, NL denotes neutral monodentate ligands and AL denotes anionic monodentate ligands (for a more detailed definition of the ligands, see below). For explanation, it should be noted that ligands L1, L2, L3 and L4 in the general formula [L1L2L3L4M1]$^{n+}$ are not necessarily identical with the ligands likewise denoted by L1 to L4 in another general formula [L1L2L3L4M1]$^{n+}$. Since, in accordance with the invention, the states leading to emission essentially result from M-M interactions, the ligands themselves do not have to contain chromophoric π systems.

Preferred structures of the oligomers to be employed in accordance with the invention are explained in greater detail below.

Columnar Structures Built Up from Singly Positively and Singly Negatively Charged Square-Planar Complexes:

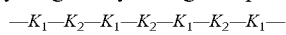

$K_1$: square-planar, singly positively charged complex
$K_2$: square-planar, singly negatively charged complex

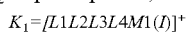

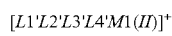

(The ligands in the second formula are marked by a prime and can/must be ligands other than the ligands without a prime in order to achieve charge compensation.)

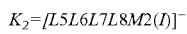

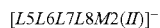

where $M1(I)/M2(I)=Ir(I),Rh(I)$ $M1(II)/M2(II)=Pt(II),Pd(II)$

The structures of the complexes and ligands L1, L2, L3, L4, L5, L6, L7 and L8 and L1', L2', L3', L4', L5', L6', L7' and L8' are explained below with reference to general formulae and with reference to examples.

Examples of double-complex salts where

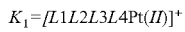

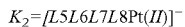

Examples of component $K_1=[L1L2L3L4Pt(II)]^+$:

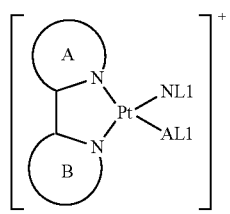

General formula for α-diimine complexes

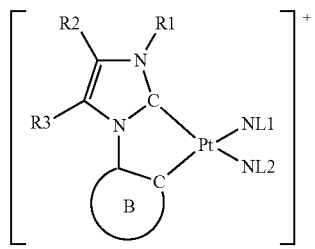

General formula for cyclometallated carbene-Pt complexes

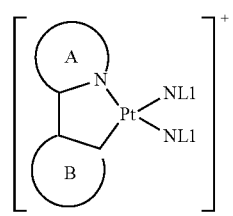

General formula for cyclometallated imine complexes where the diimine and carbene ligands, the radicals R1 to R20, NL1 to NL4 and AL1 to AL4 are defined in the "Definition of the ligands and radicals" section.

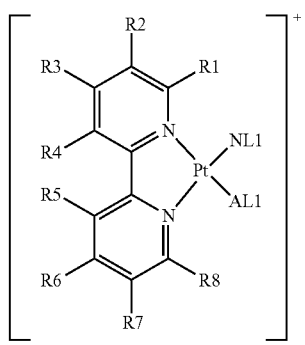

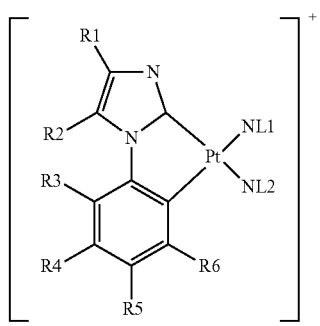

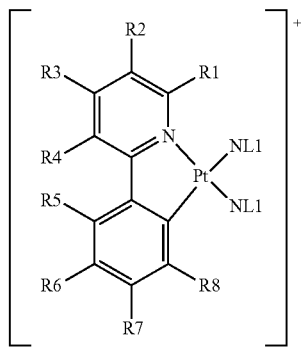

-continued
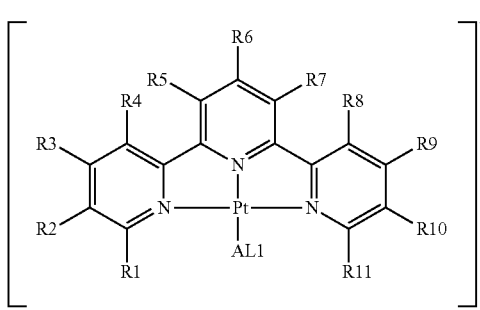
7
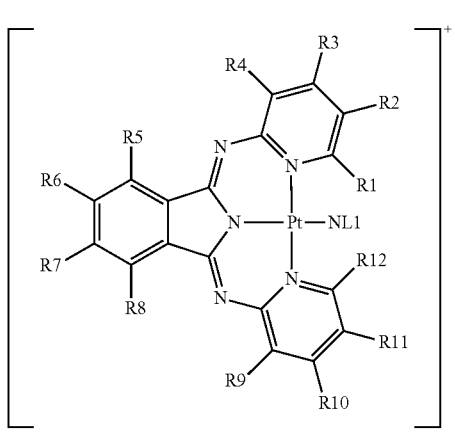
8
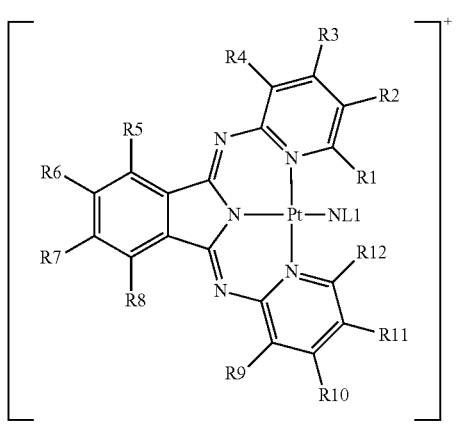
9
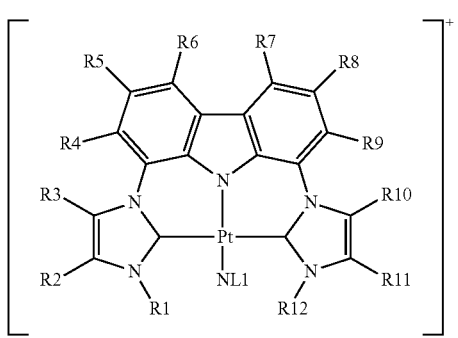
10
-continued
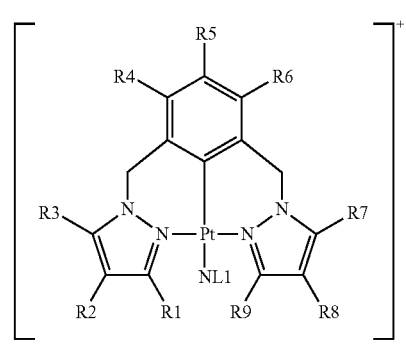
11
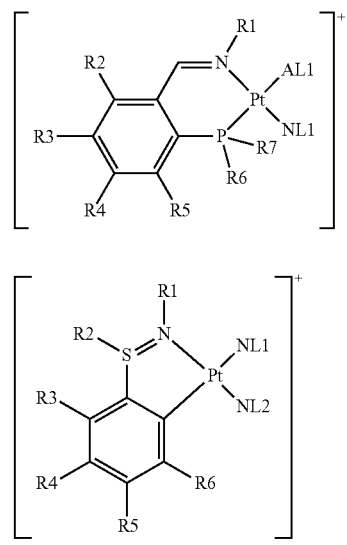
12
13
14
15

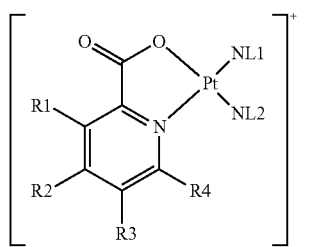
16
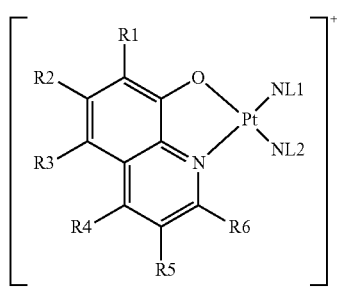
17
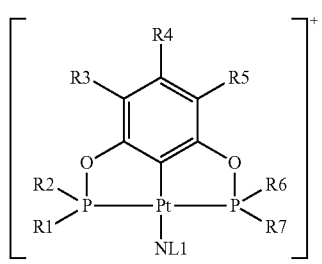
18
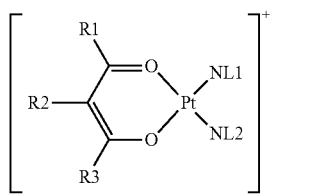
19
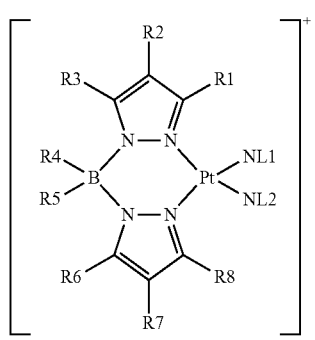
20
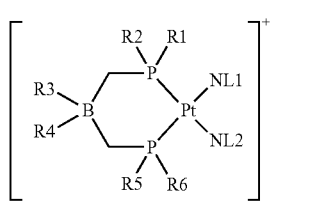
21
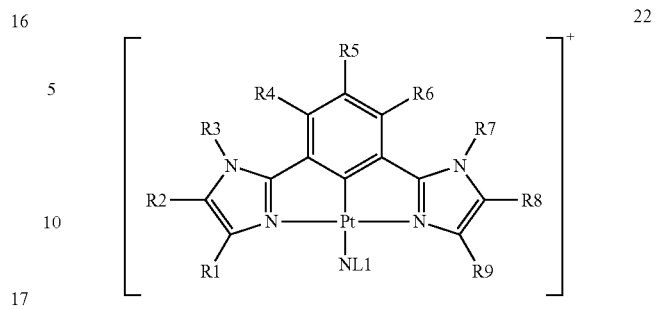
22
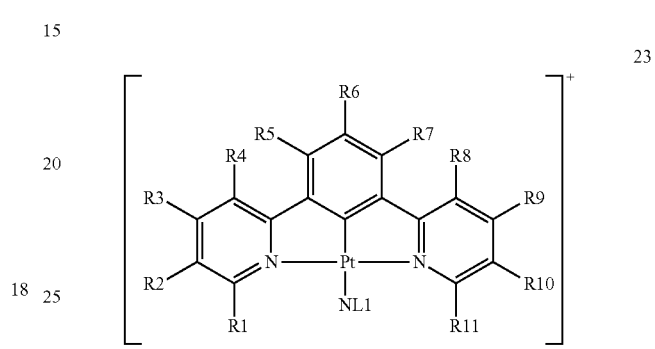
23
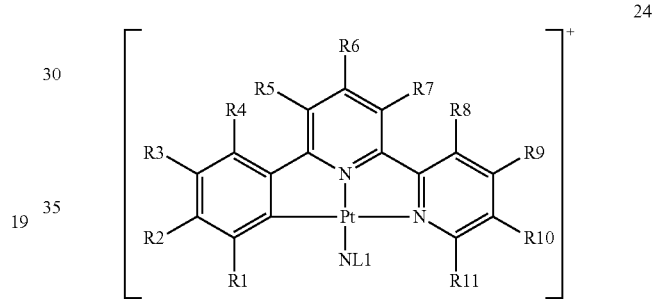
24
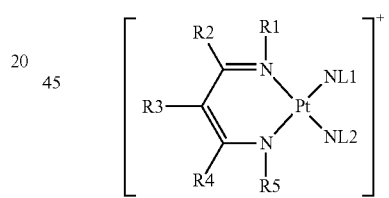
25
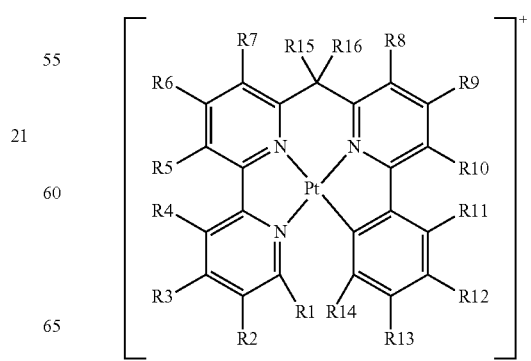
26

-continued
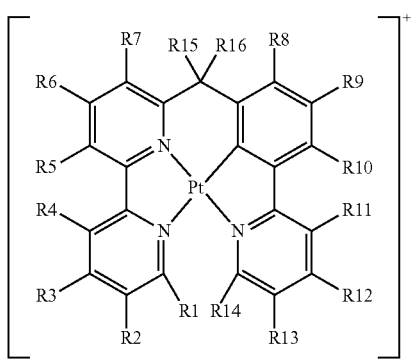
27
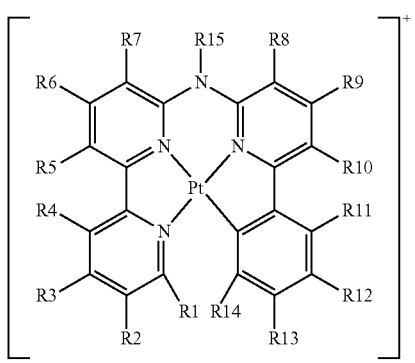
28
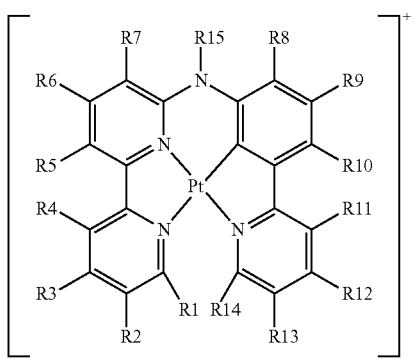
29
Examples of component K₂=[L5L6L7L8Pt(II)]⁻:
General Formulae:
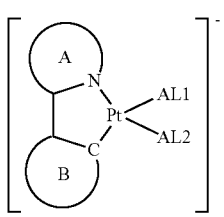
30
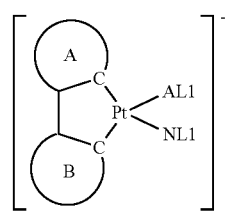
31
These formulae are defined more precisely below (see section: Definition of the ligands and radicals).
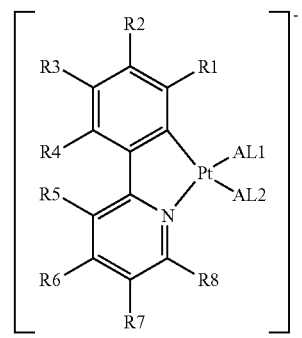
32
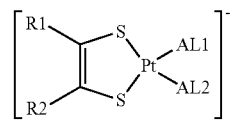
33
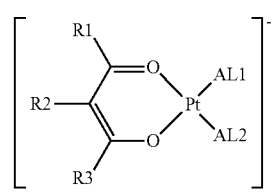
34
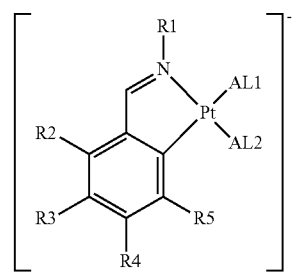
35
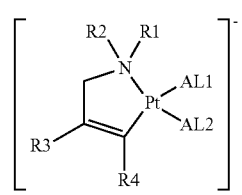
36

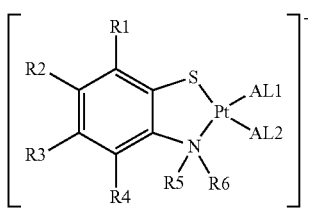
37
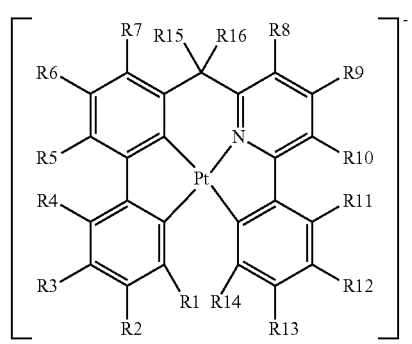
43
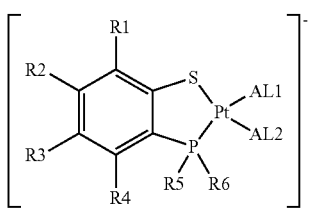
38
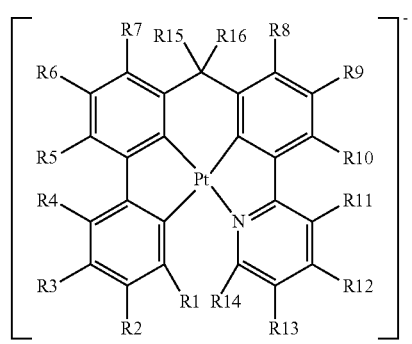
44
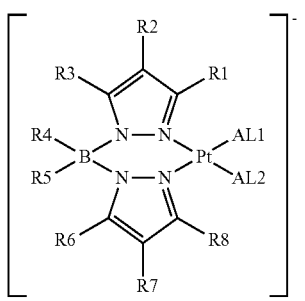
39
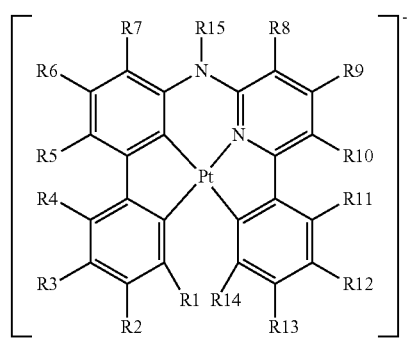
45
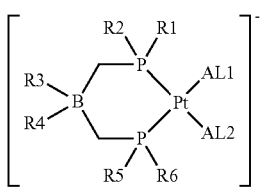
40
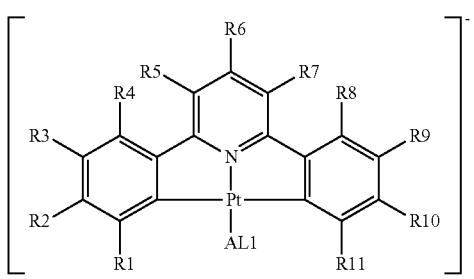
41
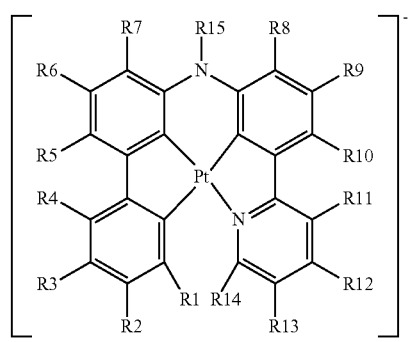
46
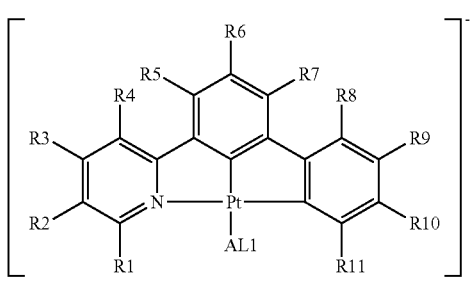
42
Examples of double-complex salts where
$K_1 = [L1L2L3L4Pd(II)]^+$
$K_2 = [L5L6L7L8Pd(II)]^-$ Examples of component $K_1=[L1L2L3L4Pd(II)]^+$:

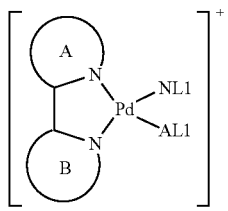

General formula for α-diimine complexes

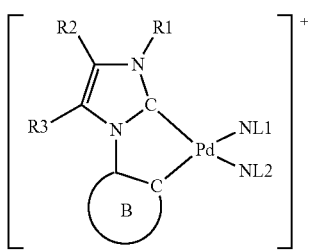

General formula for cyclo-metallatedcarbene-Pd complexes where the diimine and carbene ligands, the radicals R1 to R20, NL1 to NL4 and AL1 to AL4 are as defined herein (see section: Definition of the ligands and radicals).

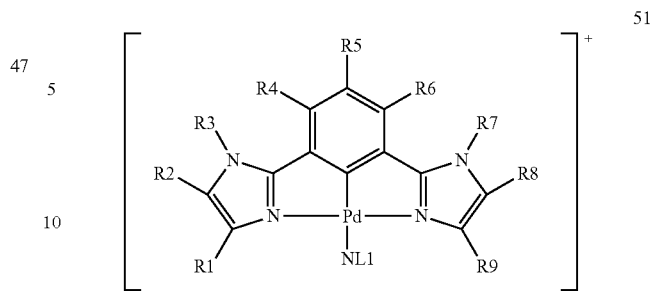

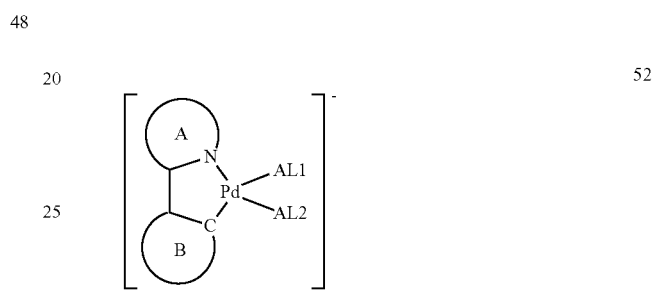

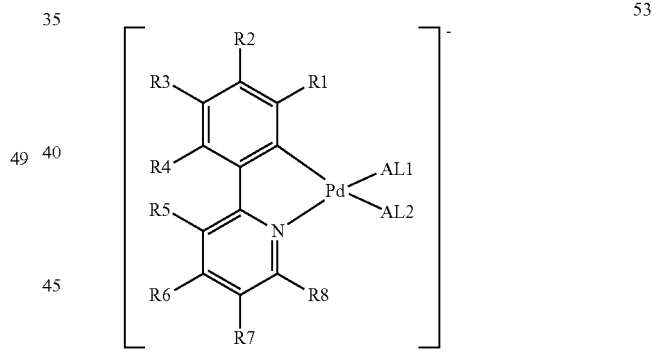

Examples of component $K_2=[L5L6L7L8Pd(II)]^-$

General Formula:

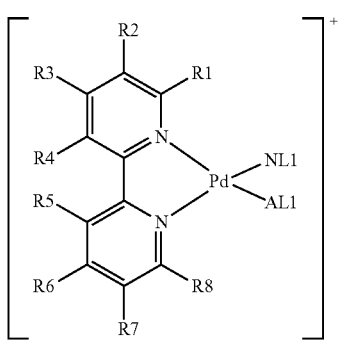

This formula is defined more precisely below (see section: Definition of the ligands and radicals).

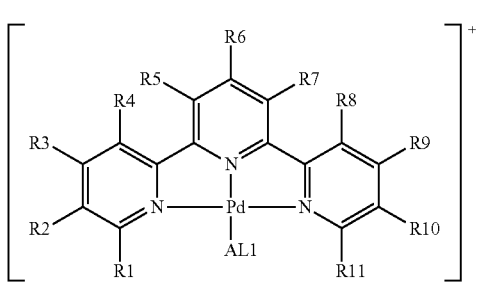

In addition to the examples of $K_1=[L1L2L3L4Pd(II)]^+$ and $K_2=[L5L6L7L8Pd(II)]^-$ shown here, all singly positively or singly negatively charged Pt complexes shown above can also be used, but Pt must be replaced with Pd.

Examples of double-complex salts where $K_1=[L1L2L3L4Ir(I)]^+$ $K_2=[L5L6L7L8Ir(I)]^-$ Examples of component $K_1=[L1L2L3L4Ir(I)]^+$:
General Formulae:
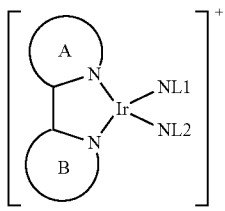
55
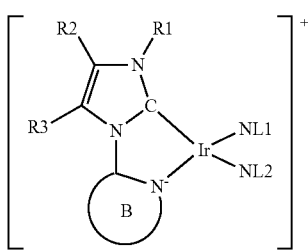
56
where the diimine and carbene ligands, the radicals R1 to R20, NL1 to NL4 and AL1 to AL4 are as defined herein (see section: Definition of the ligands and radicals).
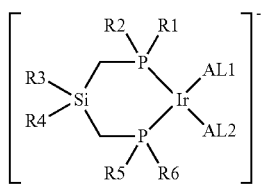
57
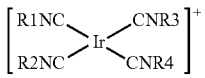
58
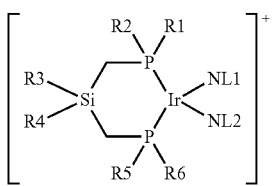
59
Examples of component $K_2=[L5L6L7L8Ir(I)]^-$:
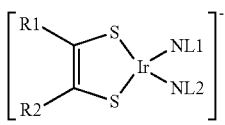
60
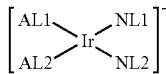
61
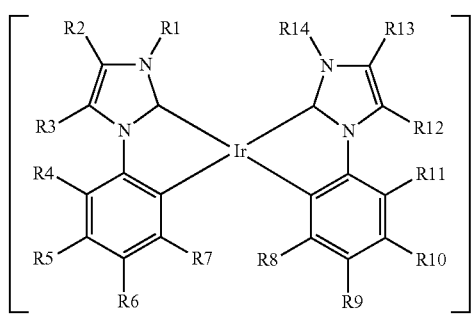
62
63
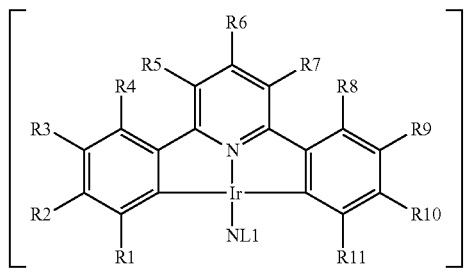
64
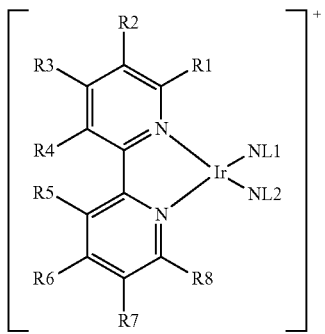
65
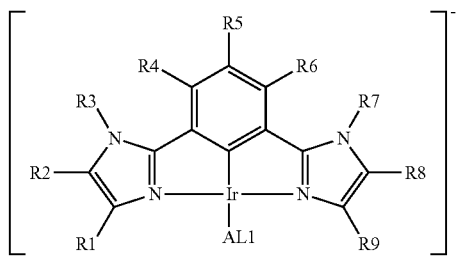
66
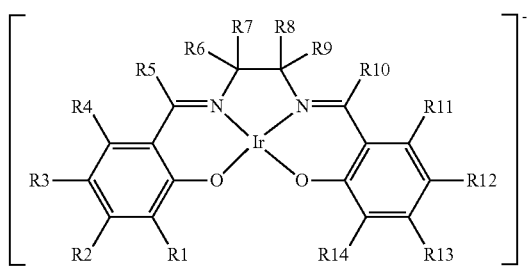

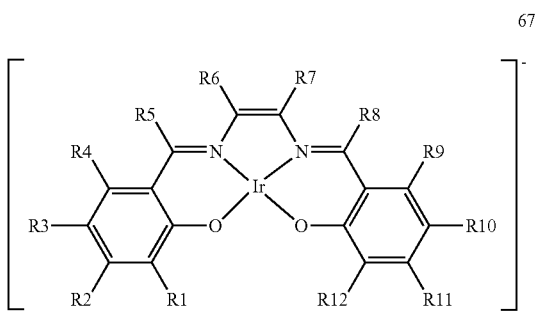
67
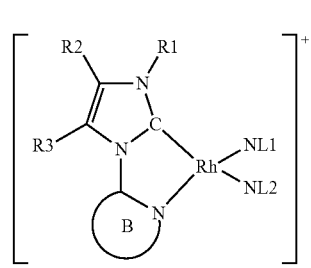
71
where the diimine and carbene ligands, the radicals R1 to R20, NL1 to NL4 and AL1 to AL4 are as defined herein (see section: Definition of the ligands and radicals).
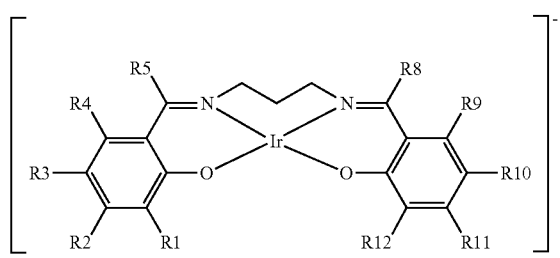
68
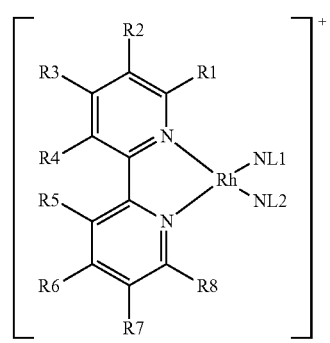
72
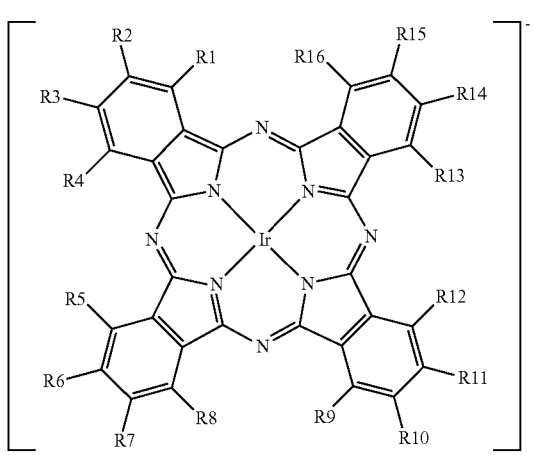
69
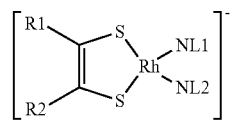
73
Examples of component $K_2=[L5L6L7L8Rh(I)]^-$:
Examples of double-complex salts where
$K_1 = [L1L2L3L4Rh(I)]^+$
$K_2 = [L5L6L7L8Rh(I)]^-$
Examples of component $K_1 = [L1L2L3L4Rh(I)]^+$:
General Formulae:
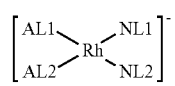
74
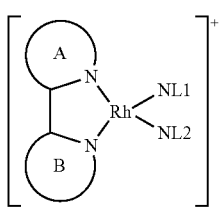
70
75
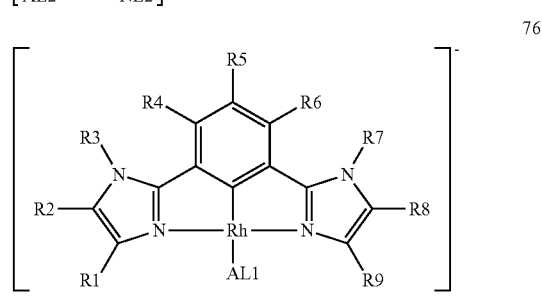
76

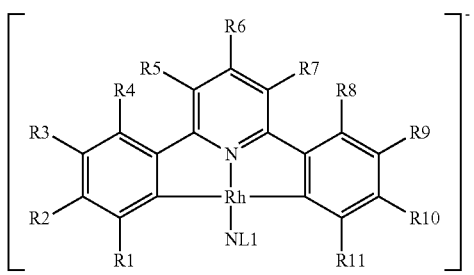

77

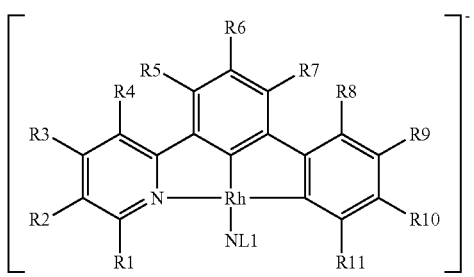

78

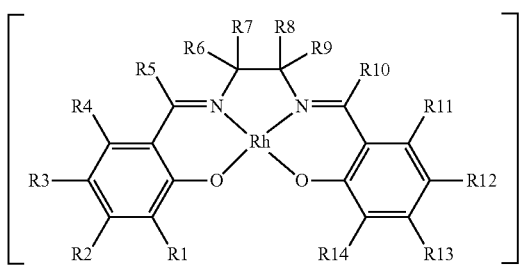

79

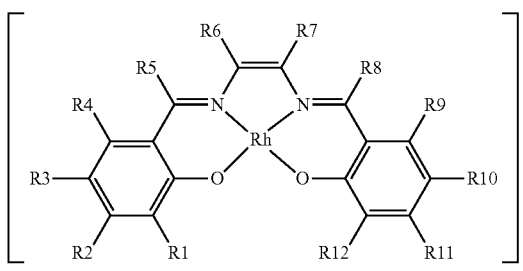

80

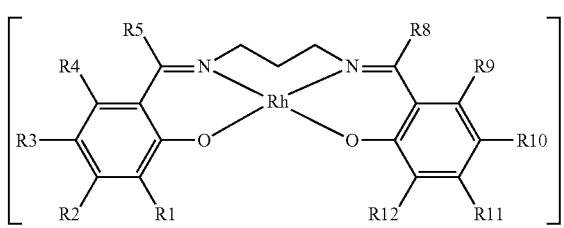

81

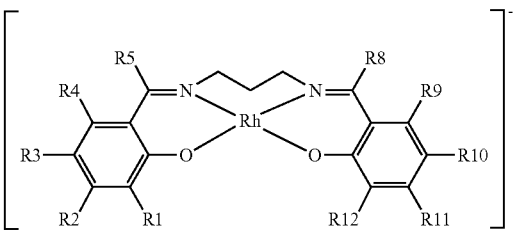

82

Columnar structures built up from doubly positively or doubly negatively charged square-planar complexes:

$$-K_1-K_2-K_1-K_2-K_1-K_2-K_1-$$

$K_1$: square-planar, doubly positively charged complex
$K_2$: square-planar, doubly negatively charged complex $$K_1 = [L1L2L3L4M1(II)]^{2+}$$

$$K_2 = [L5L6L7L8M2(II)]^{2-}$$

where $M1(II), M2(II) = Pt(II), Pd(II)$

Examples of double-complex salts where $$K_1 = [L1L2L3L4Pt(II)]^{2+}$$

$$K_2 = [L5L6L7L8Pt(II)]^{2-}$$

Examples of component $K_1 = [L1L2L3L4Pt(II)]^{2+}$:

Cationic complexes which can be used are, for example, α-diimine complexes, carbene complexes and pincer complexes, such as the complexes mentioned above, and in general square-planar platinum complexes with neutral ligands NL1-NL4.

General formulae (rings C and D are defined analogously to A and B (see below))

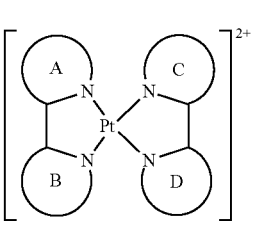

83

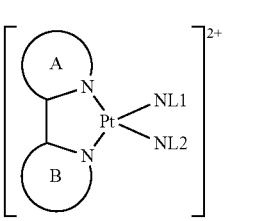

84 where the diimine ligands, the radicals R1 to R20, NL1 to NL4 and AL1 to AL4 are as defined herein (see section: Definition of the ligands and radicals).

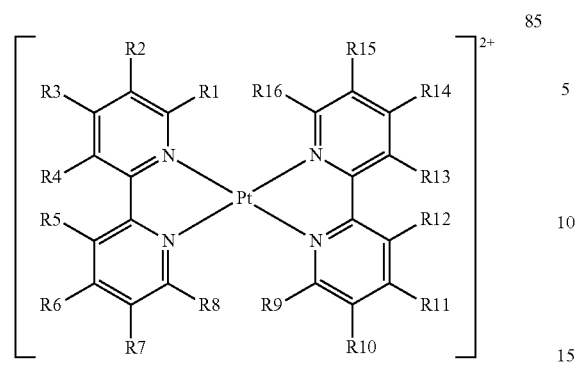
85
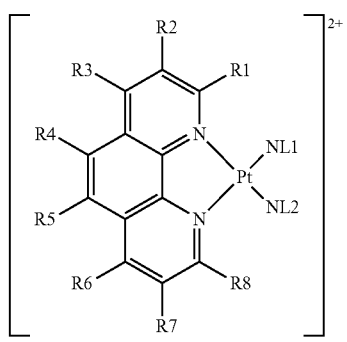
89
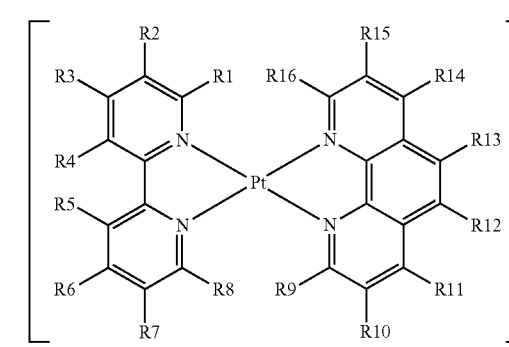
86
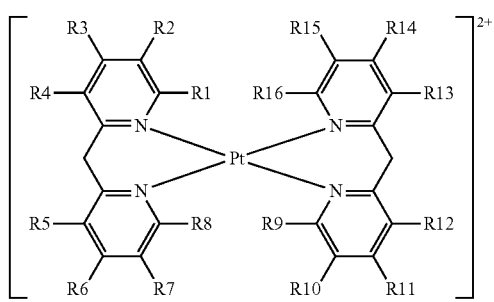
90
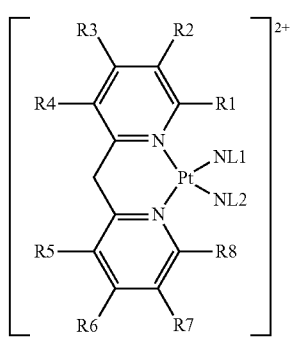
91
87
88
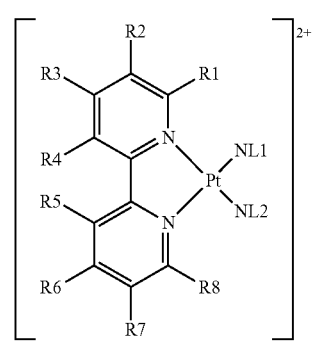
General Formulae:
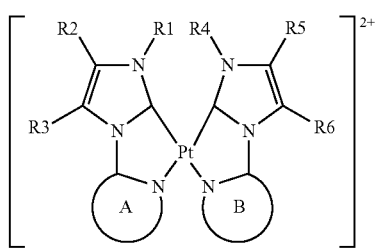
92
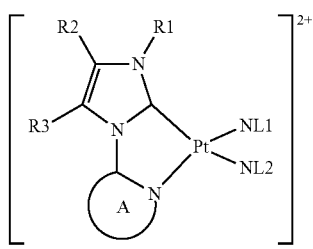
93 where carbene ligands, the radicals R1 to R20, NL1 to NL4 and AL1 to AL4 are as defined herein (see section: Definition of the ligands and radicals).
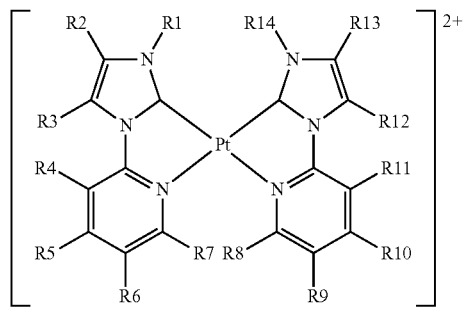
94
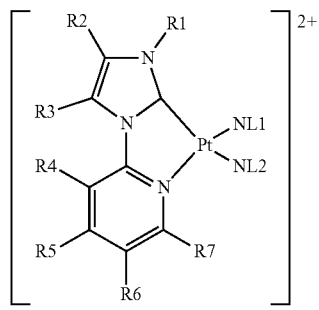
95
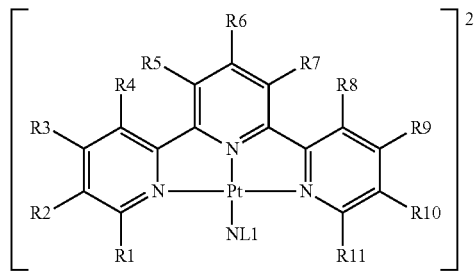
96
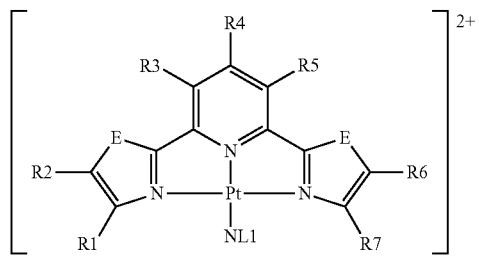
97
E = O, S, NR, where R is defined like R1 to R20)
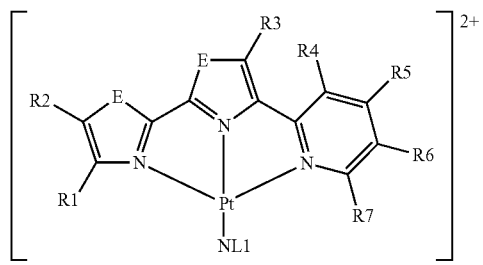
98
E = O, S, NR, where R is defined like R1 to R20)
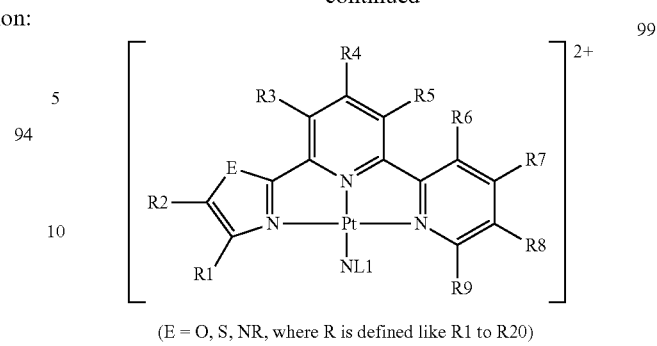
99
(E = O, S, NR, where R is defined like R1 to R20)
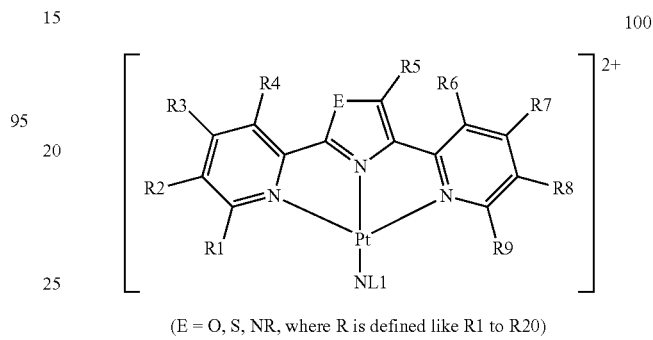
100
(E = O, S, NR, where R is defined like R1 to R20)
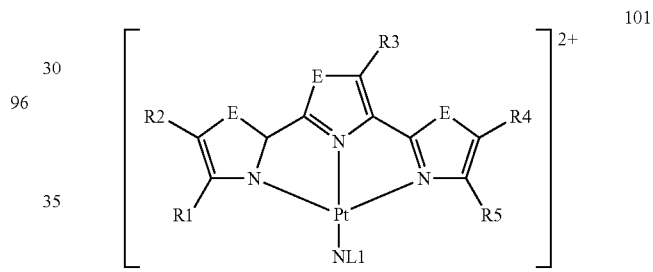
101
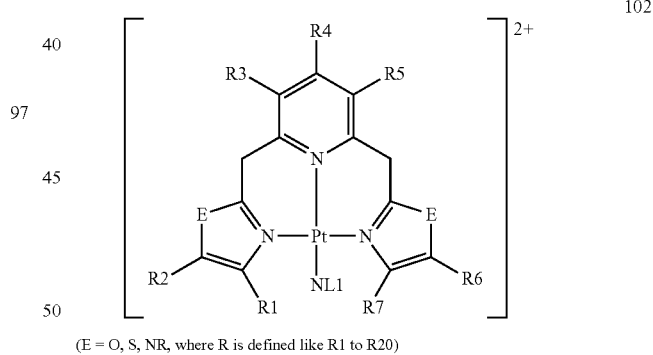
102
(E = O, S, NR, where R is defined like R1 to R20)
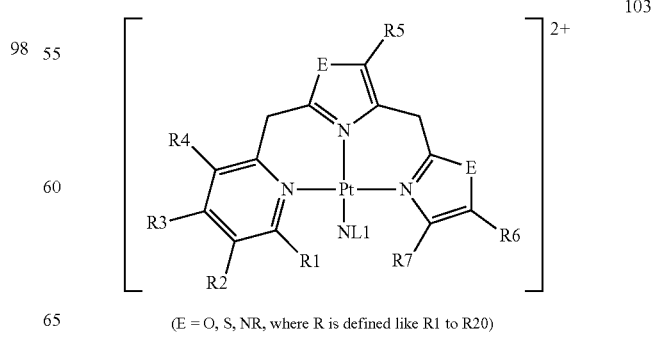
103
(E = O, S, NR, where R is defined like R1 to R20)

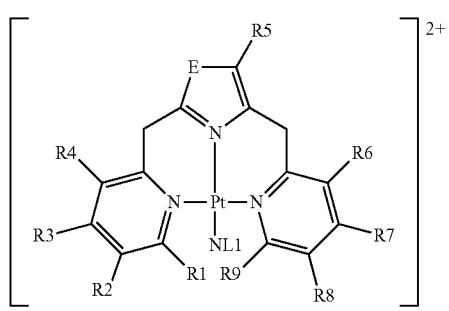
104
(E = O, S, NR, where R is defined like R1 to R20)
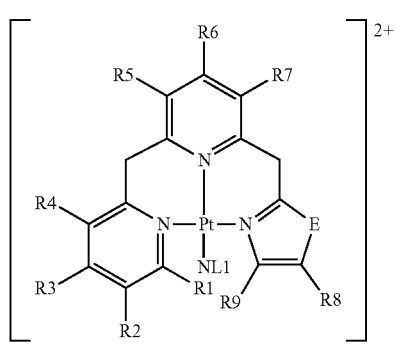
105
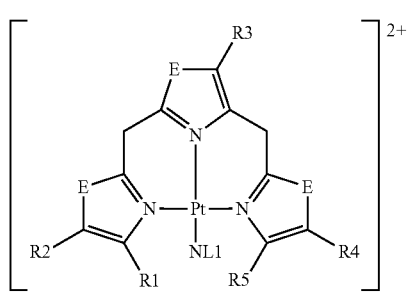
106
(E = O, S, NR, where R is defined like R1 to R20)
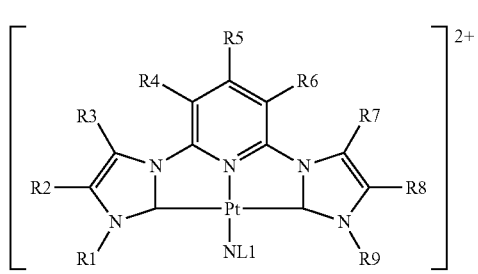
107
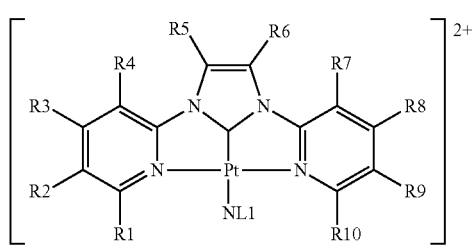
108
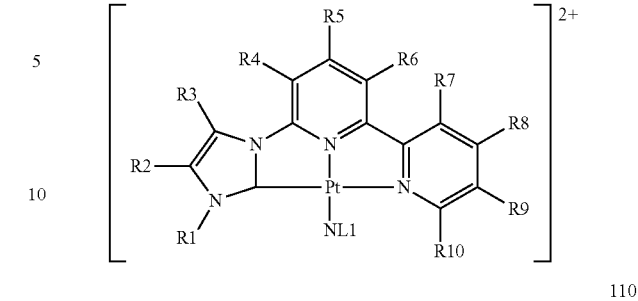
109
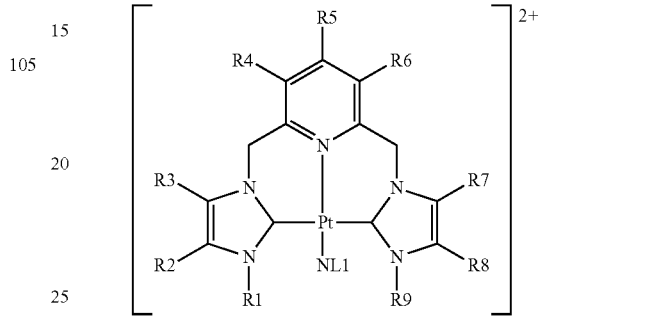
110
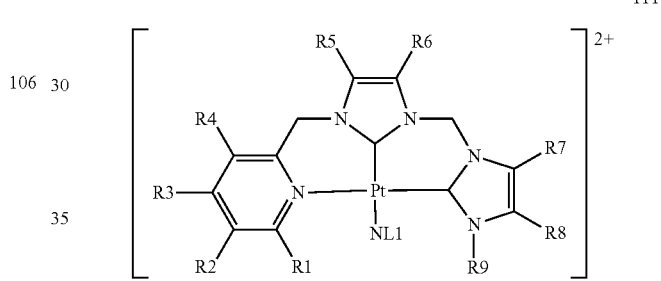
111
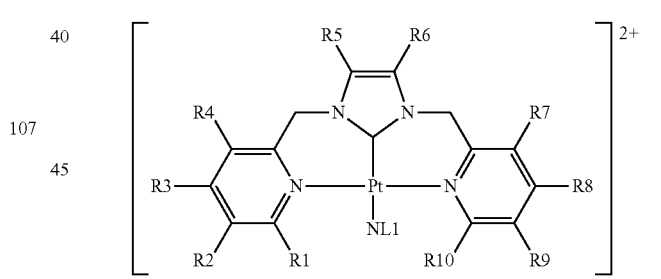
112
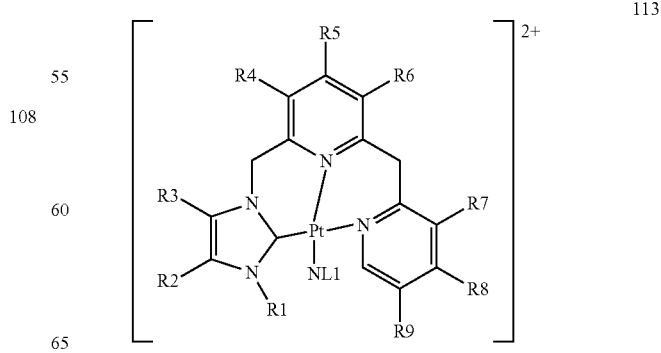
113

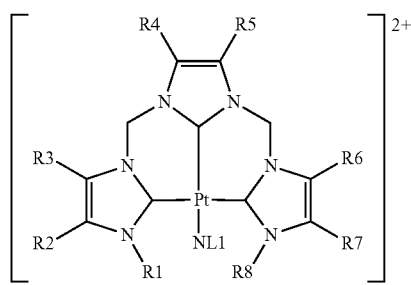
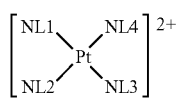
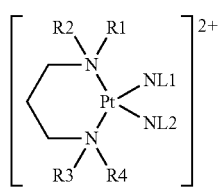
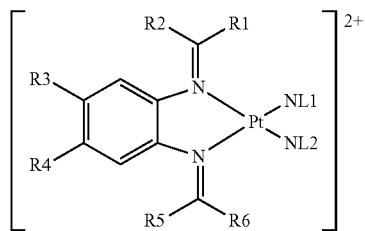
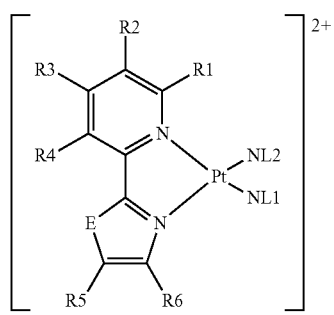
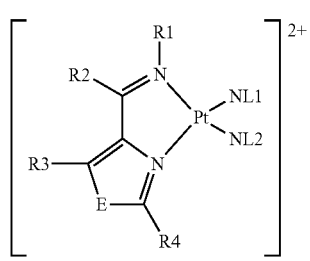
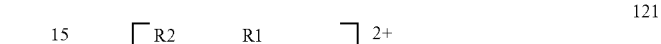
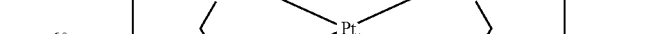

-continued
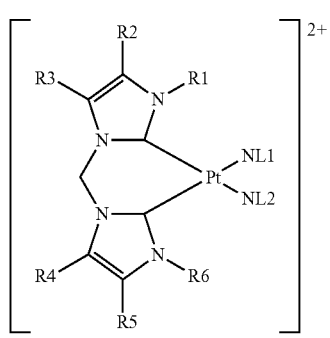
125
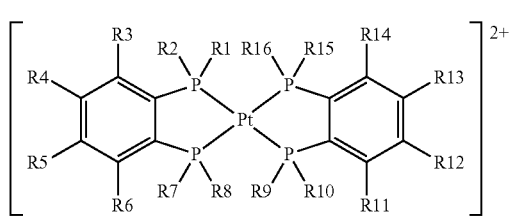
126
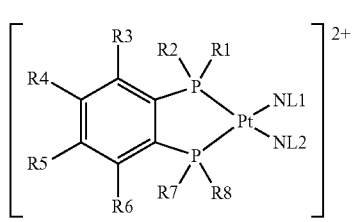
127
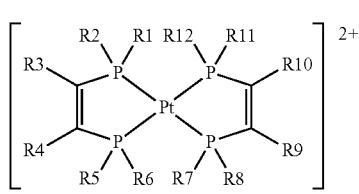
128
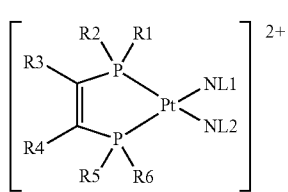
129
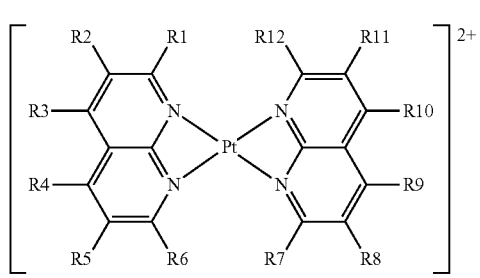
130
-continued
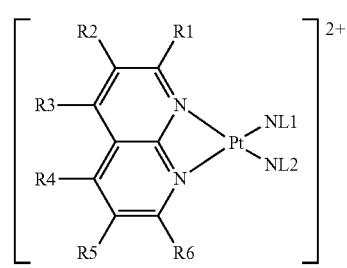
131
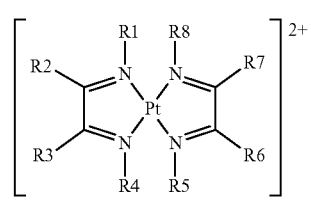
132
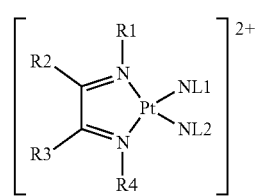
133
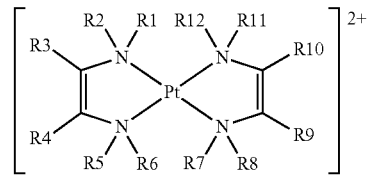
134
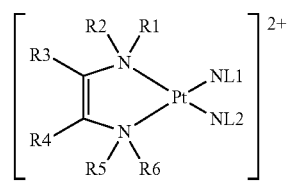
135
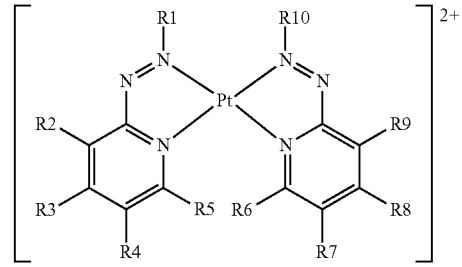
136
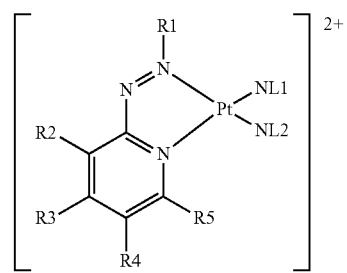
137

The complex anion used can preferably be $[Pt(CN)_4]^{2-}$.

Examples of component $K_2=[L5L6L7L8Pt(II)]^{2-}$: However, other complex anions, such as, for example, $[PtCl_4]^{2-}$, $[PtBr_4]^{2-}$, $[PtI_4]^{2-}$, $[Pt(C\equiv CR)_4]^{2-}$, $[Pt(ox)_2]^{2-}$, $[Pt(1,2\text{-dithiolate ligand})_2]^{2-}$ or $[Pt(1,1\text{-dithiolate ligand})_2]^{2-}$, which facilitate an M-M interaction, can also be employed.

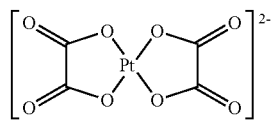

138

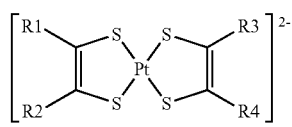

139

140

141

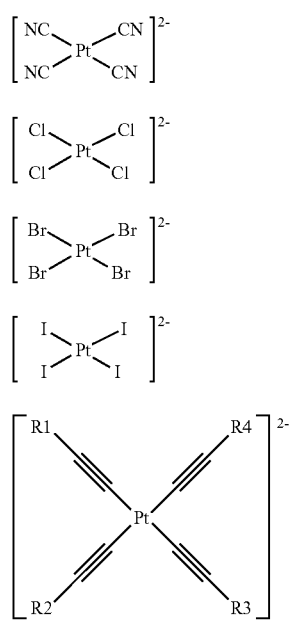

142

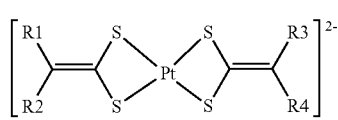

143

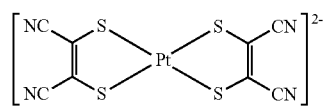

144

145

146-152 represent a series of complex anions of the general formulae (144) and (145) by way of example:

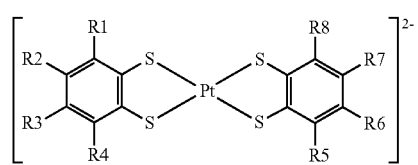

146

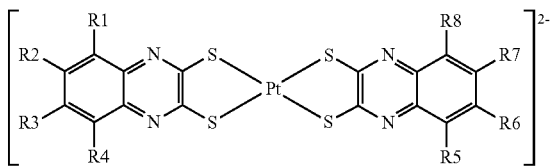

147

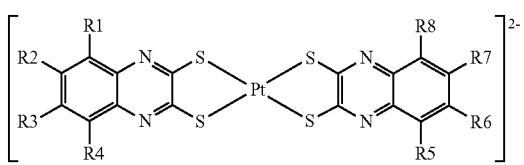

148 149

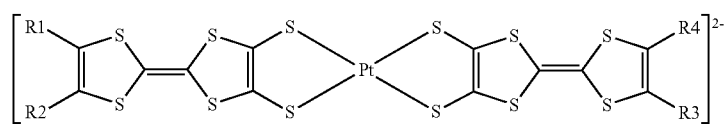

150

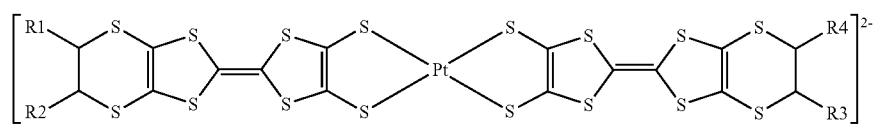

151

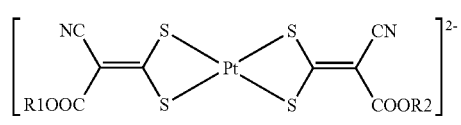

152

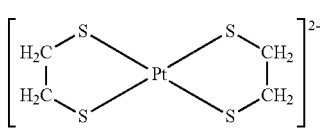

153

-continued

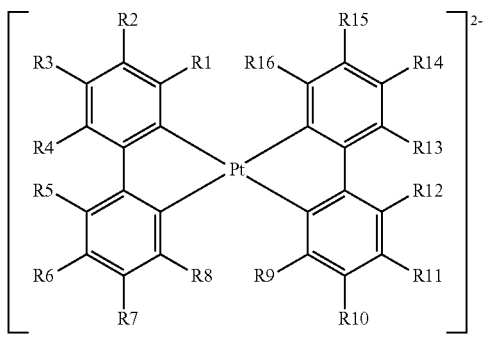

154

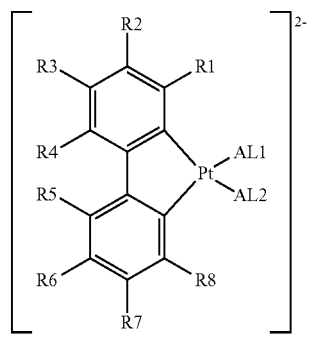

155

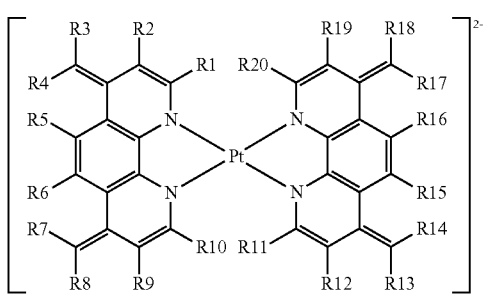

156

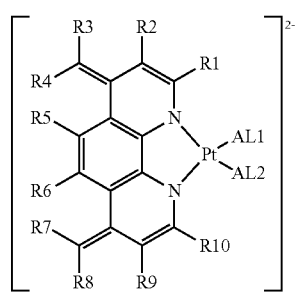

157

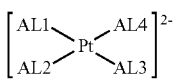

158

Examples of double-complex salts where $K_1=[L1L2L3L4Pd(II)]^{2+}$ $K_2=[L5L6L7L8Pd(II)]^{2-}$ Examples of component $K_1=[L1L2L3L4Pd(II)]^{2+}$:

Examples of doubly positively charged square-planar Pd(II) complexes which can be used are the above-mentioned examples of $K_1=[L1L2L3L4Pt(II)]^{2+}$, but Pt(II) must be replaced with Pd(II).

Examples of component $K_2=[L5L6L7L8Pd(II)]^{2-}$:

Examples of doubly negatively charged square-planar Pd(II) complexes which can be used are the above-mentioned examples of K2=[L5L6L7L8Pt(II)]$^{2-}$, but Pt(II) must be replaced with Pd(II).

Double-complex salts consisting of differently charged complexes with various central metals.

Doped Columnar Structures

—K$_1$—K$_2$—K$_1$—K$_2$-D$_1$-K$_2$—K$_1$—K$_2$—K$_1$— or

—K$_2$—K$_1$—K$_2$—K$_1$-D$_2$-K$_1$—K$_2$—K$_1$—K$_2$—

Doping of charged, square-planar Pt complexes (D), which are incorporated in low concentration into a chain of charged, square-planar Pd complexes (K$_1$, K$_2$), is also preferred. This enables the emission range of the Pt compound to be shifted. The Pd complex stack acts like a matrix which interacts with the doped Pt complex. Owing to this principle, a shift in the emission maxima occurs. The doping here can be carried out on columnar structures built up from singly or doubly charged complexes (K$_1$, K$_2$).

EXAMPLES a) K$_1$: square-planar, singly positively charged Pd complex
K$_2$: square-planar, singly negatively charged Pd complex
D$_1$: square-planar, singly positively charged Pt complex
D$_2$: square-planar, singly negatively charged Pt complex
b) K$_1$: square-planar, doubly positively charged Pd complex
K$_2$: square-planar, doubly negatively charged Pd complex
D$_1$: square-planar, doubly positively charged Pt complex
D$_2$: square-planar, doubly negatively charged Pt complex However, it is also possible to incorporate singly or doubly charged Pd complexes into columnar structures built up from singly or doubly charged Pt complexes. This enables the size of the oligomers responsible for light emission, and thus the emission wavelength, to be varied.

The concept of doping can also be applied in accordance with the invention to columnar structures built up from charged complexes of the elements Ir(I) and Rh(I). Each square-planar complex with the appropriate charge can be doped into the respective columnar structure here.

The complex employed for the doping is preferably present in the oligomer matrix in a molar ratio of at most 1:3, preferably at most 1:10, preferably at most 1:50 and in particular at most 1:100, based on the oligomer matrix-forming complexes. The complex employed for the doping is preferably present in the oligomer matrix in a molar ratio of at least 1:100 000, preferably at least 1:10 000, more preferably at least 1:1000, based on the oligomer matrix-forming complexes.

The concept explained for the doping of columnar structures can be used predominantly to control the emission colour and is for this reason of major importance for OLED applications. This applies in particular since blue or white emission light can be generated using this inventive concept. This inventive concept is distinguished, in particular, by the fact that -$D_1$-$D_1$- or -$D_2$-$D_2$- adjacent arrangements cannot arise in the construction principle according to the invention owing to the defined charge of the doped complexes, $D_1$ or $D_2$. The preferred colour blue can thus be achieved, for example.

Columnar Structures Built Up from Singly Positively/Negatively or Doubly Positively/Negatively Charged Square-Planar Complexes with Various Metal Centres:

In addition to the double-complex salts already mentioned above, double-complex salts with different metal centres in stoichiometric composition (undoped) can also arise. In a further preferred form, a further component is doped.

—$K_1$—$K_2$—$K_1$—$K_2$—$K_1$—$K_2$—$K_1$—

Examples $K_1$: square-planar, singly positively (negatively) charged complex $K_2$: square-planar, singly negatively (positively) charged complex $K_1 = [L1L2L3L4M1(I)]^+$ $[L1'L2'L3'L4'M1(II)]^+$ $K_2 = [L5L6L7L8M2(I)]^-$ $[L5'L6'L7'L8'M2(II)]^-$ where $M1(I)/M2(I) = Rh(I)$ $M1(II)/M2(II) = Pt(II), Pd(II)$ The following columnar structures, for example, arise from this:

$K_1 = [L1L2L3L4Pt(II)]^+$ $K_2 = [L5L6L7L8Pd(II)]^-$ $K_1 = [L1L2L3L4Pd(II)]^+$ $K_2 = [L5L6L7L8Pd(II)]^-$ $K_1 = [L1L2L3L4Pt(II)]^+$ $K_2 = [L5L6L7L8Ir(I)]^-$ $K_1 = [L1L2L3L4Ir(I)]^+$ $K_2 = [L5L6L7L8Pt(II)]^-$ $K_1 = [L1L2L3L4Pt(II)]^+$ $K_2 = [L5L6L7L8Rh(II)]^-$ $K_1 = [L1L2L3L4Rh(I)]^+$ $K_2 = [L5L6L7L8Pt(II)]^-$ $K_1 = [L1L2L3L4Pd(II)]^+$ $K_2 = [L5L6L7L8Ir(I)]^-$ $K_1 = [L1L2L3L4Ir(I)]^+$ $K_2 = [L5L6L7L8Pd(II)]^-$ $K_1 = [L1L2L3L4Rh(I)]^+$ $K_2 = [L5L6L7L8Pd(II)]^-$ $K_1 = [L1L2L3L4Pd(II)]^+$ $K_2 = [L5L6L7L8Rh(I)]^-$ $K_1 = [L1L2L3L4Ir(I)]^+$ $K_2 = [L5L6L7L8Rh(I)]^-$ $K_1 = [L1L2L3L4Rh(I)]^+$ $K_2 = [L5L6L7L8Ir(I)]^-$ $K_1$: square-planar, doubly positively (negatively) charged complex $K_2$: square-planar, doubly negatively (positively) charged complex $K_1 = [L1L2L3L4M1(II)]^{2+}$ $K_2 = [L5L6L7L8M2(I)]^{2-}$ $[L5'L6'L7'L8'M2(II)]^{2-}$ where $M2(I) = Ir(I), Rh(I)$ $M1(II)/M2(II) = Pt(II), Pd(II)$ The following double-complex salt columnar structures arise from this:

$K_1 = [L1L2L3L4Pt(II)]^{2+}$ $K_2 = [L5L6L7L8Pd(II)]^{2-}$ $K_1 = [L1L2L3L4Pd(II)]^{2+}$ $K_2 = [L5L6L7L8Pt(II)]^{2-}$ $K_1 = [L1L2L3L4Pt(II)]^{2+}$ $K_2 = [L5L6L7L8Ir(I)]^{2-}$ $K_1 = [L1L2L3L4Pt(II)]^{2+}$ $K_2 = [L5L6L7L8Rh(I)]^{2-}$ $K_1 = [L1L2L3L4Pd(II)]^{2+}$ $K_2 = [L5L6L8Ir(I)]^{2-}$ $K_1 = [L1L2L3L4Pd(II)]^{2+}$ $K_2 = [L5L6L7L8Rh(I)]^{2-}$

The ligands denoted by L1 to L8 and L1' to L8' in a metal-complex combination are not necessarily identical with the ligands likewise denoted by L1 to L8 and L1' to L8' in another combination.

Further Combinations:

The following types of columnar structures are also possible (examples): Complex-salt oligomer consisting of three or more different complexes:

Examples of a triple combination:

—$K_1$—$K_2$—$K_3$—$K_1$—$K_2$—$K_3$—$K_1$—

$K_1 = [L1L2L3L4M1(II)]^{2+}$ $K_2 = [L5L6L7L8M2(II)]^-$ $K_3 = [L5L6L7L8M2(II)]^+$ $K_1 = [L5L6L7L8M2(II)]^{2-}$ $K_2 = [L1L2L3L4M1(II)]^+$ $K_3 = [L1L2L3L4M1(II)]^+$ $K_1 = [L1L2L3L4M1(II)]^{2+}$ $K_2 = [L5L6L7L8M2(I)]^-$ $K_3 = [L5L6L7L8M2(I)]^-$ $K_1 = [L5L6L7L8M2(II)]^{2-}$ $K_2 = [L1L2L3L4M1(I)]^+$ $K_3 = [L1L2L3L4M1(I)]^+$

L1-L4 and L5-L8 each stand, independently, for a neutral or charged ligand, in particular for a monodentate or polydentate ligand. Ligands L1-L8 here must be selected so that the overall charge of the complex that is necessary in each case is retained. The ligands denoted by L1 to L8 and L1' to L8' in a metal-complex combination are not necessarily identical with the ligands likewise denoted by L1 to L8 and L1' to L8' in another combination.

Definition of the Ligands and Radicals

L1 to L4, L5 to L8, L9 to L12 and L1' to L12' each stand, independently, for a neutral or charged ligand, in particular for a monodentate or polydentate ligand. Ligands L1 to L12 here must be selected so that the overall charge of the complex that is necessary in each case is retained. For all embodiments described herein, solubilisation of the double-complex salts is particularly preferred. In order to increase the solubilisability, at least one of the ligands therefore particularly preferably has a large organic group, in particular one or more alkyl groups having 1 to 40 C atoms, preferably having 1 to 20 C atoms, and/or one or more polysiloxane groups ($-OSiR_2)_n-OSiR'_3$, where n=1-200, in particular n=5-30, and/or one or more polyether groups, in particular ($-OCH_2)_n-OR$ or ($-OCH_2CH_2)_n-OR$, where n=1-200, in particular n=2-30, where R is as defined herein and R' can have the meanings indicated for R, but R and R' are preferably $C_1$-$C_6$ alkyl groups.

If used herein, ligands NL1-NL4 are neutral monodentate ligands. Preferred neutral ligands are selected from carbon monoxide, isonitriles, such as, for example, tert-butyl isonitrile, cyclohexyl isonitrile, adamantyl isonitrile, phenyl isonitrile, mesityl isonitrile, 2,6-dimethylphenyl isonitrile, 2,6-diisopropylphenyl isonitrile, 2,6-di-tert-butylphenyl isonitrile, amines, such as, for example, trimethylamine, triethylamine, morpholine, phosphines, such as, for example, trifluorophosphine, trimethylphosphine, tricyclohexyl-phosphine, tri-tert-butylphosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(penta-fluorophenyl)arsine, stibines, such as, for example, trifluorostibine, trimethylstibine, tricyclohexylstibine, tri-tert-butylstibine, triphenylstibine, tris(pentafluorophenyl)stibine, and nitrogen-containing heterocycles, such as, for example, pyridine, pyridazine, pyrazine, pyrimidine, triazine. For example, it is also possible to use nitriles or isonitriles which are substituted by a large organic group R' or R" (R' and R" defined like R1-R20). However, suitable neutral ligands are also compounds which coordinate via N, P, S, O, As or Se.

If used herein, ligands AL1-AL4 represent anionic monodentate ligands. Preferred anionic ligands are selected from hydride, deuteride, the halides F, Cl, Br and I, alkylacetylides, such as, for example, methyl-C≡C$^-$, tert-butyl-C≡C$^-$, arylacetylides, such as, for example, phenyl-C≡C$^-$, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-butanethiolate, thiophenolate, amides, such as, for example, dimethylamide, diethylamide, diisopropylamide, morpholide, carboxylates, such as, for example, acetate, trifluoroacetate, propionate, benzoate, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. Aryl groups, alkenyl groups or borates are furthermore possible.

α-Diimine ligands, as used herein, can consist both of five- or six-membered rings, whose constituents Z1-Z12 are either the fragments CR(X) (R(X)=see definition of R1-R20) or N, E can be either NR, O or S. This definition also includes the possibility that the units A and B do not form a ring, but instead are open-chain. ("#" denotes the atom which is bonded to the second unit):

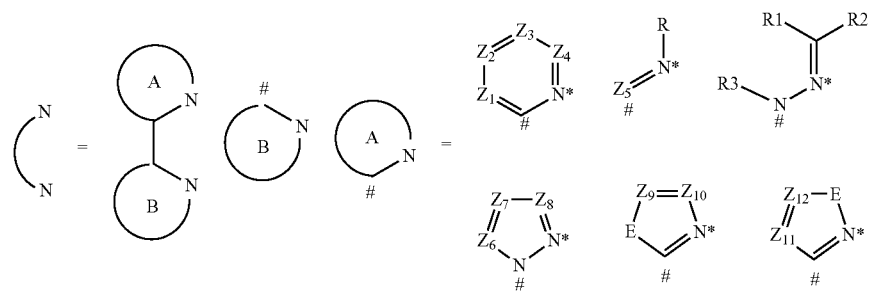

If used herein, the term carbene ligand denotes, in particular:

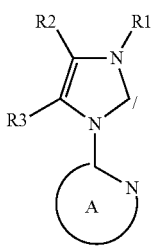

Cyclometallating ligands, if used herein, are bidentate, singly negatively charged ligands which 1) bond on the one hand via an sp² carbon atom and on the other hand via a nitrogen atom. The units A and B can consist both of five- or six-membered rings, and can be open-chain. The constituents Z1-Z26 consist either of the fragment CR(X)(R(X)=organic radical defined like R1-R20) or N, E can be either NR, O or S. ("*" denotes the atom which forms the complex bond, "#" denotes the atom which is bonded to the second unit):

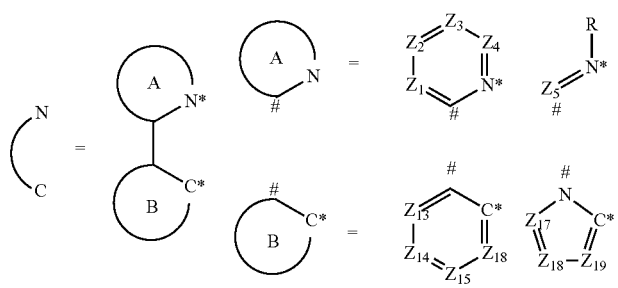

2) bond on the one hand via an sp² carbon atom and on the other hand via a carbene carbon atom. The unit B can consist of a five- or six-membered ring, but can also be open-chain. The constituents Z13-Z26 consist either of the fragment CR(X)(R(X)=organic radical like R1-R20, see below) or N, E can be NR, O or S. ("*" denotes the atom which forms the complex bond, "#" denotes the atom which is bonded to the second ring):

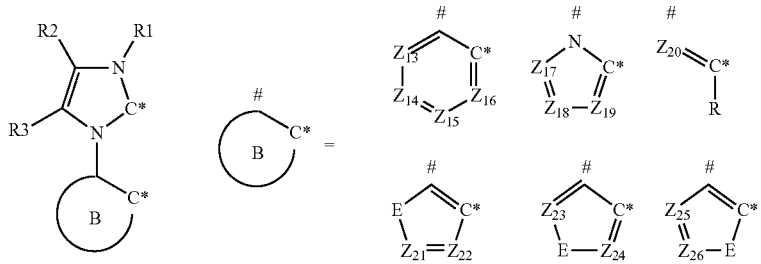

In the formulae indicated herein, R1-R20, R, R' and R" are groups which may be identical to or independent of one another. These groups are, in particular, selected from: H, deuterium, F, Cl, Br, I, N(R$^{21}$)$_2$, CN, NO$_2$, Si(R$^{21}$)$_3$, B(OR$^{21}$)$_2$, C(=O)R$^{21}$, P(=O)(R$^{21}$)$_2$, S(=O)R$^{21}$, S(=O)$_2$R$^{21}$, OSO$_2$R$^{21}$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^{21}$, where one or more non-adjacent CH$_2$ groups may be replaced by R$^{21}$C=CR$^{21}$, C=O, Si(R$^{21}$)$_2$, Ge(R$^{21}$)$_2$, Sn(R$^{21}$)$_2$, C=O, C=S, C=Se, C=NR$^{21}$, P(=O) (R$^{21}$), SO, SO$_2$, NR$^{21}$, O, S or CONR$^{21}$ and where one or more H atoms may be replaced by F, Cl, Br, I, CN or NO$_2$, or an aromatic or heteroaromatic ring system having 5 to 60 aromatic ring atoms, which may in each case be substituted by one or more radicals R$^{21}$, or an aryloxy or heteroaryloxy group having 5 to 60 aromatic ring atoms, which may be substituted by one or more radicals R$^{21}$, or a diarylamino group, diheteroarylamino group or arylheteroarylamino group having 10 to 40 aromatic ring atoms, which may be substituted by one or more radicals R$^{21}$, or a combination of these systems; two or more of these substituents may also form a mono- or polycyclic, aliphatic, aromatic and/or benzo-fused ring system with one another;

R$^{21}$ is on each occurrence, identically or differently, H, F or an aliphatic, aromatic and/or heteroaromatic hydrocarbon radical having 1 to 20 C atoms, in which, in addition, one or more H atoms may be replaced by F;

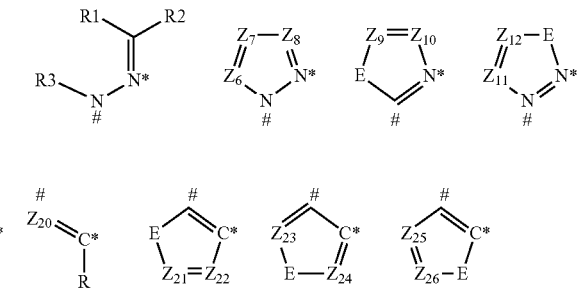

two or more substituents R$^{21}$ here may also form a mono- or polycyclic, aliphatic or aromatic ring system with one another.

In order to guarantee solubility, long-chain, also branched alkyl chains (C$_1$-C$_{30}$) and short-chain polyethers [for example polymers (—OCH$_2$CH$_2$O—)$_n$, n<500] are preferred. The alkyl chains may also be modified with polar groups, for example with alcohols, aldehydes, amines, carboxylic acids, ethers, phosphoric acid esters, phosphonic acids, which facilitate a further increase in the solubility.

R(X) herein stands for organic groups (analogously to the definition of R1-R20), which may be identical to or independent of one another. X is a serial number and serves for numbering of the radical R (for example R(1), R(2), . . . ). The organic groups can be selected, in particular, from the groups as described above for R1 to R20.

Alkyl radicals as described herein denote, in particular, $C_1$-$C_{30}$—, preferably $C_1$-$C_{20}$—, particularly preferably $C_1$-$C_6$-alkyl radicals. Alkyl radicals may also form a ring.

Alkenyl and alkynyl radicals preferably have 2 to 30, in particular 2 to 20, particularly preferably 2 to 8, C atoms.

Aryl groups are preferably systems having 5 to 30, in particular 5 to 10, ring atoms, where 0 to 4 heteroatoms selected from O, N, P and/or S are preferably present.

The ligand units A and/or B, defined in general terms above, of the α-diimine ligands, carbene ligands and cyclo-metallating ligands may also be bridged by NL and/or AL.

TABLE 1

Some examples of double-complex salts which can be employed in accordance with the invention in OLEDs

| Compound | Absorption [nm] | Emission [nm] |
|---|---|---|
| [Pt(bpy)$_2$][Pt(CN)$_4$] red-orange | 330, 520 (dr) | 620 |
| [Pt(bpy)$_2$][Pt(CN)$_4$] × 2 H$_2$O yellow-orange | 485 (dr) | 570 |
| [Pt(phen)$_2$][Pt(CN)$_4$] violet | 310, 380, 550 (dr) | 650 |
| [Pt(phen)$_2$][Pt(CN)$_4$] × H$_2$O violet | into the yellow spectral region | 628 |
| [Pt(bpy)(en)][Pt(CN)$_4$] pale yellow | 330, 450 (dr) | 560 |
| [Pt(phen)(en)][Pt(CN)$_4$] pale yellow | 310, 430 (dr) | 560 |
| [Pt(4,4'-dimethyl-2,2'-dipyridyl)$_2$][Pt(CN)$_4$] | 354, 418, 474 | 544 |

(dr) diffuse reflectance

TABLE 2

Some specific examples of novel double-complex salts, combinations, dopings

Compound

[Pd(bpy)$_2$][Pt(CN)]$_4$
[Pt(bpy)$_2$][Pd(CN)]$_4$
[Pd(bpy)$_2$][Pd(CN)]$_4$
[Pd(phen)$_2$][Pt(CN)$_4$]
[Pt(phen)$_2$][Pd(CN)$_4$]
[Pd(phen)$_2$][Pd(CN)$_4$]
{[Pd(bpy)$_2$][Pd(CN)$_4$]$_{1-x}$[Pt(CN)$_4$]$_x$}; 0.00001 ≤ x ≤ 0.99999
{[Pd(bpy)$_2$][Pt(CN)$_4$]$_{1-x}$[Pd(CN)$_4$]$_x$}; 0.00001 ≤ x ≤ 0.99999
{[Pt(bpy)$_2$][Pd(CN)$_4$]$_{1-x}$[Pt(CN)$_4$]$_x$}; 0.00001 ≤ x ≤ 0.99999
{[Pt(bpy)$_2$][Pt(CN)$_4$]$_{1-x}$[Pd(CN)$_4$]$_x$}; 0.00001 ≤ x ≤ 0.99999
{[Pd(CNR)$_4$][Pd(CN)$_4$]$_{1-x}$[Pt(CN)$_4$]$_x$}; 0.00001 ≤ x ≤ 0.99999
{[Pd(CNR)$_4$][Pt(CN)$_4$]$_{1-x}$[Pd(CN)$_4$]$_x$}; 0.00001 ≤ x ≤ 0.99999
{[Pt(CNR)$_4$][Pd(CN)$_4$]$_{1-x}$[Pt(CN)$_4$]$_x$}; 0.00001 ≤ x ≤ 0.99999
{[Pt(CNR)$_4$][Pt(CN)$_4$]$_{1-x}$[Pd(CN)$_4$]$_x$}; 0.00001 ≤ x ≤ 0.99999
[Pd(CNR)$_4$][Pt(CN)$_4$]
[Pt(CNR)$_4$][Pd(CN)$_4$]
[Pt(CNR)$_4$][Pt(CN)$_4$]
[Pd(CNR)$_4$][Pd(CN)$_4$]
[Pt(bpy)(en)][Pd(CN)$_4$]
[Pd(bpy)(en)][Pt(CN)$_4$]
[Pd(bpy)(en)][Pd(CN)$_4$]
[Pt(phen)(en)][Pd(CN)$_4$]
[Pd(phen)(en)][Pt(CN)$_4$]
[Pd(phen)(en)][Pd(CN)$_4$]
[Pt(CNCH$_3$)$_4$][Pd(CN)$_4$]
[Pd(CNCH$_3$)$_4$][Pt(CN)$_4$]
[Pt(CNCH$_3$)$_4$][Pt(CN)$_4$]
[Pd(CNCH$_3$)$_4$][Pd(CN)$_4$]
[Pt(CNC$_2$H$_5$)$_4$][Pd(CN)$_4$]
[Pd(CNC$_2$H$_5$)$_4$][Pt(CN)$_4$]
[Pt(CNC$_2$H$_5$)$_4$][Pt(CN)$_4$]
[Pd(CNC$_2$H$_5$)$_4$][Pd(CN)$_4$]
[Pt(CN-t-C$_4$H$_9$)$_4$][Pd(CN)$_4$]

TABLE 2-continued

Some specific examples of novel double-complex salts, combinations, dopings

Compound

[Pd(CN-t-C$_4$H$_9$)$_4$][Pt(CN)$_4$]
[Pt(CN-t-C$_4$H$_9$)$_4$][Pt(CN)$_4$]
[Pd(CN-t-C$_4$H$_9$)$_4$][Pd(CN)$_4$]
[Pt(CN-cyclododecyl)$_4$][Pd(CN)$_4$]
[Pd(CN-cyclododecyl)$_4$][Pt(CN)$_4$]
[Pt(CN-cyclododecyl)$_4$][Pt(CN)$_4$]
[Pd(CN-cyclododecyl)$_4$][Pd(CN)$_4$]
[Pt(phen)(CN-cyclohexyl)$_2$][Pd(CN)$_4$]
[Pd(phen)(CN-cyclohexyl)$_2$][Pt(CN)$_4$]
[Pt(phen)(CN-cyclohexyl)$_2$][Pt(CN)$_4$]
[Pd(phen)(CN-cyclohexyl)$_2$][Pd(CN)$_4$]
[Pt(CN-n-tetradecyl)$_4$][Pd(CN)$_4$]
[Pd(CN-n-tetradecyl)$_4$][Pt(CN)$_4$]
[Pt(CN-n-tetradecyl)$_4$][Pt(CN)$_4$]
[Pd(CN-n-tetradecyl)$_4$][Pt(CN)$_4$]
{[Pt(phen)(CN-cyclododecyl)Cl]$_2$[Pt(phen)(CN-cyclododecyl)$_2$]$_2$[Pd(CN)$_4$]$_3$}
{[Pd(phen)(CN-cyclododecyl)Cl]$_2$[Pd(phen)(CN-cyclododecyl)$_2$]$_2$[Pt(CN)$_4$]$_3$}
{[Pt(phen)(CN-cyclododecyl)Cl]$_2$[Pd(phen)(CN-cyclododecyl)$_2$]$_2$[Pt(CN)$_4$]$_3$}
{[Pd(phen)(CN-cyclododecyl)Cl]$_2$[Pt(phen)(CN-cyclododecyl)$_2$]$_2$[Pt(CN)$_4$]$_3$}
{[Pt(phen)(CN-cyclododecyl)Cl]$_2$[Pd(phen)(CN-cyclododecyl)$_2$]$_2$[Pd(CN)$_4$]$_3$}
{[Pd(phen)(CN-cyclododecyl)Cl]$_2$[Pt(phen)(CN-cyclododecyl)$_2$]$_2$[Pd(CN)$_4$]$_3$}
{[Pt(phen)(CN-cyclododecyl)Cl]$_2$[Pt(phen)(CN-cyclododecyl)$_2$]$_2$[Pt(CN)$_4$]$_3$}
{[Pd(phen)(CN-cyclododecyl)Cl]$_2$[Pd(phen)(CN-cyclododecyl)$_2$]$_2$[Pd(CN)$_4$]$_3$}
[Pt(p-CN—C$_6$H$_4$—C$_{10}$H$_{21}$)$_4$][Pd(CN)$_4$]
[Pd(p-CN—C$_6$H$_4$—C$_{10}$H$_{21}$)$_4$][Pt(CN)$_4$]
[Pt(p-CN—C$_6$H$_4$—C$_{10}$H$_{21}$)$_4$][Pt(CN)$_4$]
[Pd(p-CN—C$_6$H$_4$—C$_{10}$H$_{21}$)$_4$][Pd(CN)$_4$]
[Pt(p-CN—C$_6$H$_4$—CH$_3$)$_4$][Pd(CN)$_4$]
[Pd(p-CN—C$_6$H$_4$—CH$_3$)$_4$][Pt(CN)$_4$]
[Pt(p-CN—C$_6$H$_4$—CH$_3$)$_4$][Pt(CN)$_4$]
[Pd(p-CN—C$_6$H$_4$—CH$_3$)$_4$][Pd(CN)$_4$]
[Pt(p-CN—C$_6$H$_4$—C$_6$H$_{13}$)$_4$][Pd(CN)$_4$]
[Pd(p-CN—C$_6$H$_4$—C$_6$H$_{13}$)$_4$][Pt(CN)$_4$]
[Pt(p-CN—C$_6$H$_4$—C$_6$H$_{13}$)$_4$][Pt(CN)$_4$]
[Pd(p-CN—C$_6$H$_4$—C$_6$H$_{13}$)$_4$][Pd(CN)$_4$]
[Pt(p-CN—C$_6$H$_4$—C$_{10}$H$_{21}$)$_4$][Pd(CN)$_4$]
[Pd(p-CN—C$_6$H$_4$—C$_{10}$H$_{21}$)$_4$][Pt(CN)$_4$]
[Pt(p-CN—C$_6$H$_4$—C$_{10}$H$_{21}$)$_4$][Pt(CN)$_4$]
[Pd(p-CN—C$_6$H$_4$—C$_{10}$H$_{21}$)$_4$][Pd(CN)$_4$]
[Pt(p-CN—C$_6$H$_4$—C$_{12}$H$_{25}$)$_4$][Pd(CN)$_4$]
[Pd(p-CN—C$_6$H$_4$—C$_{12}$H$_{25}$)$_4$][Pt(CN)$_4$]
[Pt(p-CN—C$_6$H$_4$—C$_{12}$H$_{25}$)$_4$][Pt(CN)$_4$]
[Pd(p-CN—C$_6$H$_4$—C$_{12}$H$_{25}$)$_4$][Pd(CN)$_4$]
[Pt(p-CN—C$_6$H$_4$—C$_{14}$H$_{29}$)$_4$][Pd(CN)$_4$]
[Pd(p-CN—C$_6$H$_4$—C$_{14}$H$_{29}$)$_4$][Pt(CN)$_4$]
[Pt(p-CN—C$_6$H$_4$—C$_{14}$H$_{29}$)$_4$][Pt(CN)$_4$]
[Pd(p-CN—C$_6$H$_4$—C$_{14}$H$_{29}$)$_4$][Pd(CN)$_4$]

CNR denotes common isonitrile ligands.

The oligomers described herein are eminently suitable for use in opto-electronic components, in particular of OLEDs. All oligomers or columnar structures described herein can be used in the manufacture of OLEDs. The emission colour desired in each case can be achieved through suitable choice of the oligomers. In order to achieve blue emission, doped oligomers are preferably employed.

Owing to the opposite charges of the metal complex employed in accordance with the invention, the electrostatic interaction (ionic bonding) results in pronounced stabilisation of the M-M bond, to which, inter alia, the very poor solubility of such compounds is attributable. Although this fact significantly simplifies synthesis, since the double-complex salts usually precipitate instantaneously on combination of the respectively soluble components, it makes, however, more detailed analysis and the various applications more difficult. Since vacuum sublimation is usually unsuitable for salts owing to their low volatility, wet-chemical methods (for example spin coating, printing) remain for the production of thin layers, as are necessary for OLEDs. However, these themselves require a certain solubility of the compounds. However, this does not apply if the double-complex salts are employed as dispersions or if the process of introduction by diffusion is selected. (See the comments under "Processing of the double-complex salts in OLEDs".)

Luminescent platinum double-complex salts of the general formula $[L1L2L3L4Pt]^{2+}[Pt(AL1)_4]^{2-}$ are generally insoluble. In this example, ligands L1-L4 are neutral. L1-L4 can also be bonded to one another, i.e. form polydentate ligands. In this case, they form complexes which, for example, contain either a) one bidentate and two monodentate ligands, b) two bidentate ligands, c) one tridentate and one monodentate ligand or d) one tetradentate ligand. For example, the neutral ligands can be α-diimines, such as 2,2'-bipyridine or 1,10-phenanthroline, and AL1 can be a cyanide, chloride, bromide or iodide ion. Owing to their excellent photophysical properties, these double-complex salts are, in accordance with this invention, good candidates for opto-electronic applications (OLEDs).

Solubilisation as Processing Technique

Surprisingly, double-complex salts can now be modified in such a way that they either dissolve as oligomers or, in polar solvents, also as ions. The subject-matter of this invention utilises the fact that, although the bonds within the complex stack are strong owing to the M-M interactions, only weak van-der-Waals interactions essentially exist, however, between these stacks. Surprisingly, substitution at the periphery of the ligands by large organic radicals R does not hinder the M-M interactions, but disrupts the arrangement of the various columns in such a way that they no longer line up easily as crystal lattice. The substitution here can be carried out at the positively charged complexes or also at the negatively charged units. Substitution at both is also possible. Solubility can thus be achieved. The examples indicated herein are intended to illustrate the construction principles to be protected for use in opto-electronic arrangements, without restricting the general validity of the concept.

The oligomers in accordance with the present invention can also be employed in combination with a matrix material. Suitable as matrix material are various materials as used in accordance with the prior art as matrix materials for phosphorescent compounds. Suitable matrix materials are aromatic ketones, aromatic phosphine oxides or aromatic sulfoxides or sulfones, for example in accordance with WO 04/013080, WO 04/093207, WO 06/005627 or the unpublished application DE 102008033943.1, tri-arylamines, carbazole derivatives, for example CBP (N,N-biscarbazolyl-biphenyl) or the carbazole derivatives disclosed in WO 05/039246, US 2005/0069729, JP 2004/288381, EP 1205527 or WO 08/086851, indolo-carbazole derivatives, for example in accordance with WO 07/063754 or WO 08/056746, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with the unpublished application DE 102008036982.9, WO 07/063754 or WO 08/056746, zinc complexes, for example in accordance with EP 652273 or WO 09/062578, diazasilole or tetraazasilole derivatives, for example in accordance with the unpublished application DE 102008056688.8, diazaphosphole derivatives, for example in accordance with the unpublished application DE 102009022858.6, or indenocarbazole derivatives, for example in accordance with the unpublished applications DE 102009023155.2 and DE 102009031021.5.

For example, good power efficiencies can be achieved in a typical OLED layer structure consisting of an ITO anode, a hole conductor (for example comprising PEDOT/PSS), the emitter layer according to the invention, optionally a hole-blocking layer, an electron-conductor layer, a thin LiF or CsF interlayer for improving electron injection, and a metal electrode (cathode). These various layers having a total thickness of a few 100 nm can be applied, for example, to a glass substrate or another support material. A corresponding sample device is depicted in FIG. 3.

1. The support material used can be glass or any other suitable solid or flexible transparent material.
2. ITO=indium tin oxide.
3. PEDOT/PSS=polyethylenedioxythiophene/polystyrenesulfonic acid. This is a hole-conductor material (HTL=hole transport layer), which is water-soluble.
4. Emitter layer, frequently abbreviated to EML, comprising emitter substances according to the invention. The compounds can be dissolved, for example, in organic solvents, through the use of the complex units rendered soluble by suitable chemical solubilisation (method A) or by mixing-in/washing-in of the double-complex salt dispersion (method B) or by the technique of introduction by diffusion (method C). By selecting suitable organic solvents, dissolution of the underlying PEDOT/PSS layer can be avoided. The oligomers/columnar structures mentioned herein are particularly preferably present in this layer in an amount of 5% by weight to 100% by weight, depending on the application. The non-solubilisable oligomers/columnar structures according to the invention can also be introduced in an emitter matrix material (for example PVK=polyvinylcarbazole or CBP=4,4'-bis(9-carbazolyl)biphenyl) as dispersions. However, they can also be applied as 100% layer in the form of a dispersion. This manufacturing variant can be employed if the oligomers/columnar structures are not sufficiently soluble or are even insoluble.
5. ETL=electron-transport material. For example, $Alq_3$, which can be applied by vapour deposition, can be used. Thickness, for example, 40 nm.
6. The very thin interlayer comprising, for example, CsF or LiF reduces the electron-injection barrier and protects the ETL layer. This layer is generally applied by vapour deposition. For a further simplified OLED structure, the ETL and CsF layers can optionally be omitted.
7. The conductive cathode layer is applied by vapour deposition. Al represents an example. Mg:Ag (10:1) or other metals can also be used.

The voltage over the device is, for example, 3 to 15 V.

A further aspect of the invention is an opto-electronic device, in particular a light-emitting device, comprising (i) an anode, (ii) a cathode and (iii) an emitter layer, arranged between and in direct or indirect contact with the anode or cathode, comprising at least one oligomer as defined herein.

The opto-electronic devices according to the invention are manufactured by wet-chemical methods.

Processing of the Double-Complex Salts in OLEDs

The processing/use of the double-complex salts in the optically relevant layers, i.e. the emission layer in the OLED, is not obvious (simple) since the double-complex salts are very sparingly soluble or even insoluble. Surprisingly, the materials in opto-electronic components can now be processed in three different procedures:

Solubilisation:

Solubilisation of the components renders the salts readily soluble, but they nevertheless retain the favourable optical properties. This is achieved by selecting a specific embodiment, at least for one of the organic groups on the ligands. In particular, long-chain—also branched—alkyl chains ($C_1$-$C_{30}$) and short-chain polyethers [for example polymers (—$OCH_2CH_2O$—)$_n$, n<500] can preferably be used in order to guarantee solubility. The alkyl chains may also be modified with polar groups, for example with alcohols, aldehydes, amines, carboxylic acids, ethers, phosphoric acid esters, phosphonic acids, which facilitate a further increase in the solubility.

Dispersions:

For the use according to the invention of the double-complex salts, which are sparingly soluble or insoluble, the application can be carried out in the form of dispersions—preferably nanodispersions. Colloidal nanodispersions of the double-complex salts can be applied mixed or washed into a polymer solution. The concentration of the double-complex salts in the polymer is 2 to 10% by weight or 10 to 90% by weight. However, it is also possible to apply the pure double-complex salts (i.e. without polymer) as nanodispersions—dispersed in a suitable medium—and thus to achieve 100% emitter layers after evaporation of the medium. If necessary, the double-complex salts can be dispersed in the liquid phase by methods familiar to the person skilled in the art before introduction into the polymer(s) with ultrasound treatment. In addition, the double-complex salts can be generated with the action of ultrasound, by introduction of the first component and addition of the second, third, . . . component. A surface modification of the nanoparticles can optionally be carried out by addition of dispersants known to the person skilled in the art. Depending on the choice of dispersant(s), the stabilisation of the nanodispersion can be of a steric, electrical or electro-steric nature. Particularly suitable dispersants are aliphatic, aromatic or heteroaromatic amines, phosphines, sulfides, sulfoxides, sulfonic acids, carboxylic acids, aminocarboxylic acids and thiocarboxylic acids. In a particular embodiment, complex salts which carry solubilising groups, such as the above-mentioned compound [Pt(4,4'-dinonyl-2,2'-dipyridyl)$_2$][$BF_4$]$_2$, can be employed as dispersants for the double-complex salts according to the invention. The nanodisperse double-complex salts are then preferably introduced into the polymer after filtration through micro/nanofilters in order to remove relatively coarse particles which remain. This also applies to the application as 100% emitter layer.

C Diffusion Method

The novel diffusion method, proposed here for the first time, is suitable in the production of the emission layers for the use according to the invention of the insoluble or sparingly soluble oligomers/columnar structures. Firstly, one of the generally soluble components of the double-complex salts is introduced into the optically relevant polymer layer. The second component is then applied to this layer. The second component migrates through the polymer layer by diffusion to the first component, where it forms the insoluble oligomer. The method is stopped when the desired double-complex salt concentration has been reached by washing off the second complex salt component.

Advantages of the Invention for OLEDs Through the Use of Columnar Structure-Forming Double-Complex Salts:

The problems that arise in the production of efficient OLEDs have already been mentioned above. A specific change in the emission properties has now successfully been achieved through the use of the metal complexes discussed in detail above, as a result of which many of these disadvantages no longer arise. Compared with the emitter materials used in conventional OLEDs, the following advantages arise on use of the oligomers/columnar structures according to the invention:

i) The possibility of variation of the M-M separations in the oligomers/columnar structures and the possibility of variation of the average chain length of these oligomers/columnar structures enable the emission wavelengths to be controlled virtually as desired, from the blue to the red spectral region.

ii) Blue emission can be achieved in a simple manner if use is made of the concept of doping columnar structures which has already been explained above (for example Pt complexes in low concentration in oligomers/columnar structures built up from Pd complexes).

iii) In addition, the emission lifetime of the double-complex salt stacks is short, which represents a very important requirement of OLEDs.

iv) On use of the oligomers/columnar structures mentioned here, it is possible to use high current densities.

v) The oligomers/columnar structures being used here have particularly high emission quantum yields.

vi) The oligomers/columnar structures according to the invention can be regarded as one-dimensional semiconductors. Accordingly, structures of this type exhibit very high exciton mobilities.

vii) A further essential property arises through the fact that the oligomer/columnar structure double-complex salts to be employed in accordance with the invention in opto-electronic devices have very good charge-carrier mobilities. The M-M interactions raise the HOMO energetically and lower the LUMO energetically. Furthermore, the two molecular orbitals are delocalised electronically over a large number of molecules (units of the oligomers/columnar structures). This also results in a significant improvement in the hole and electron mobility. As a consequence, the emission layer (emitter layer, EML) does not require any additional components for improving the mobility, i.e. the partly restrictive requirements of the matrix with respect to good charge-carrier mobility can be dropped on use of these double-complex salts in many applications. It is thus possible to achieve a large increase in efficiency and less expensive manufacture of OLEDs.

viii) A further essential property arises through the fact that the double-complex salts are particularly stable chemically and photochemically and are thus particularly suitable for use as OLED emitters.

The invention is described in greater detail by the following examples, without wishing to restrict it thereby. The person skilled in the art will be able to carry out the invention throughout the range disclosed, without being inventive, and thus produce further organic electroluminescent devices according to the invention.

EXAMPLES

Example of a Synthesis of a Soluble Pt Double-Complex Salt: [Pt(4,4'-dinonyl-2,2'-dipyridyl)$_2$][Pt(CN)$_4$]

The concept of solubilisation of metal-metal double-complex salts will be illustrated with reference to the example of the insoluble double-complex salt [Pt(bpy)$_2$][Pt(CN)$_4$]. By the specific use of bipyridines substituted in the 4,4'-position by a CH$_3$(CH$_2$)$_8$-alkyl group in each case, it is possible to solubilise the unsubstituted, insoluble compound.

Synthetic Procedure for [Pt(4,4'-dinonyl-2,2'-dipyridyl)$_2$][BF$_2$

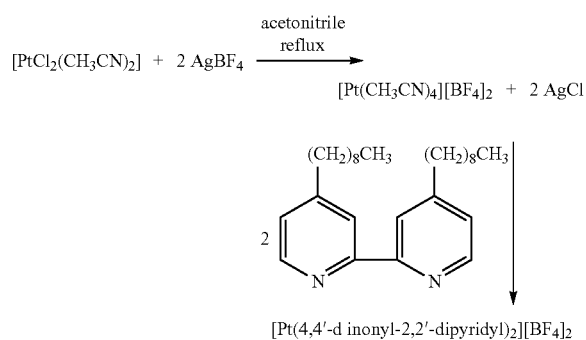

The synthesis is carried out in accordance with a modified literature procedure (cf. A. Boixasse, J. Pons, X. Solans, M. Fontbardia, J. Ros, *Inorg. Chim. Acta* 2004, 357, 827).

[PtCl$_2$(CH$_3$CN)$_2$] (0.300 g, 0.862 mmol) is suspended in 50 ml of dry acetonitrile under N$_2$. AgBF$_4$ (0.336 g, 1.724 mmol) is added, and the reaction mixture is refluxed for 20 h. Precipitated AgCl is filtered off, and 4,4'-dinonyl-2,2'-dipyridyl (0.705 g, 1.724 mmol) is added to the clear, colourless solution. The mixture is then refluxed for a further 20 h. The precipitated solid (residues of AgCl) is filtered off, and the clear, pale-yellow reaction solution is concentrated in a rotary evaporator. The solution is placed in the freezer overnight, during which a beige solid precipitates out. The precipitate is filtered off with suction and washed with ethanol and ether, and subsequently dried. The solid is dissolved in dichloromethane and precipitated using ether. The fine, pale-green precipitate is filtered off and dried in a desiccator.

Empirical formula: PtC$_{56}$H$_{88}$N$_4$B$_2$F$_8$ (1185.67 g/mol)
Elemental analysis: PtC$_{56}$H$_{88}$N$_4$B$_2$F$_8$ (1185.67 g/mol)
calculated: C, 56.68; H, 7.48; N, 4.72.
found: C, 56.68; H, 7.16; N, 4.56.
Mass spectrometry: ES-MS, m/e=506.0 M$^{2+}$, 100%

Synthetic Procedure for [Pt(4,4'-dinonyl-2,2'-dipyridyl)$_2$][Pt(CN)$_4$]

[Pt(4,4'-dinonyl-2,2'-dipyridyl)$_2$][BF$_4$]$_2$ + [n-Bu$_4$N]$_2$[Pt(CN)$_4$]

↓ dichloromethane

[Pt(4,4'-dinonyl-2,2'-dipyridyl)$_2$][Pt(CN)$_4$] + 2 [n-Bu$_4$N][BF$_4$]

[Pt(4,4'-dinonyl-2,2'-dipyridyl)$_2$][BF$_4$]$_2$ (0.0209 g, 0.0176 mmol) and [n-Bu$_4$N]$_2$[Pt(CN)$_4$] (0.0138 g, 0.0176 mmol) are dissolved separately in 4 ml of dichloromethane in each case. The two solutions are subsequently combined. The solvent is allowed to evaporate off slowly overnight, giving a yellow solid. This is washed with acetonitrile (3 ml) and dried in a desiccator.

Empirical formula: Pt$_2$C$_{60}$H$_{88}$N$_8$.CH$_2$Cl$_2$ (1396.48 g/mol)
Elemental analysis: Pt$_2$C$_{60}$H$_{88}$N$_8$.CH$_2$Cl$_2$ (1396.48 g/mol)
calculated: C, 54.95; H, 6.76; N, 8.54.
found: C, 52.46; H, 6.50; N, 8.02.

Figure 2:
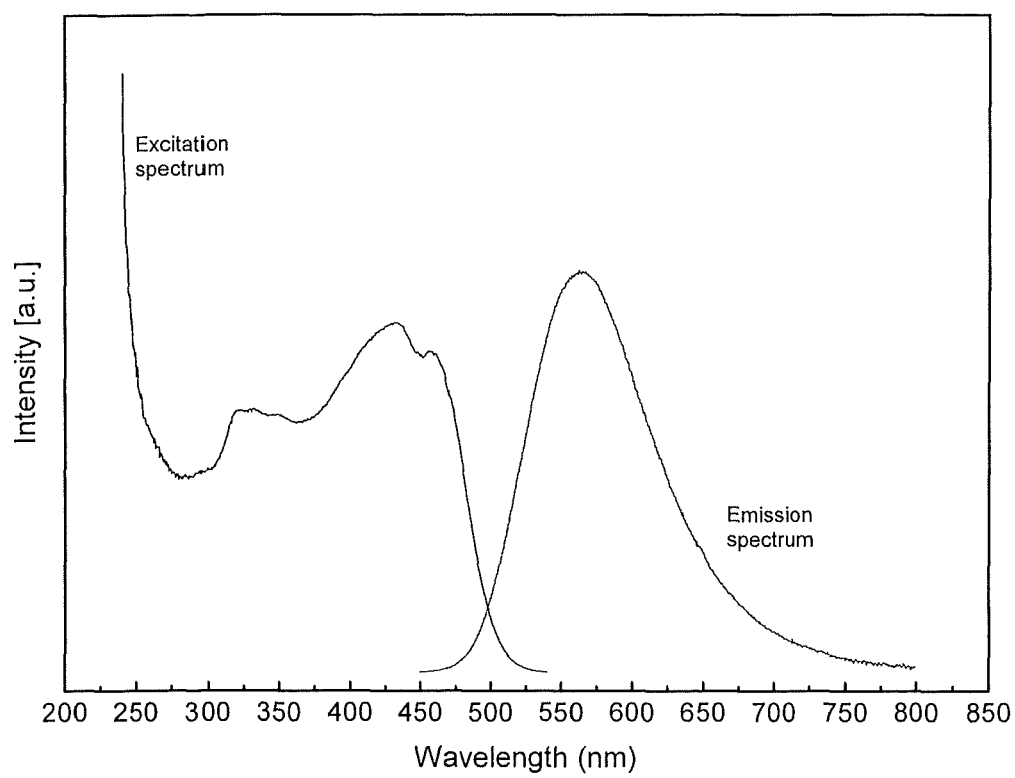
FIG. 2 shows excitation and emission spectrum of [Pt(4,4'-dinonyl-2,2'-dipyridyl)$_2$][Pt(CN$_4$)] (T=300 K, $\lambda_{exc.}$=365 nm, $\lambda_{det.}$=563 nm).

FIG. 2 shows the optical excitation spectrum and the emission spectrum of this novel substance.

Solution of [Pt(4,4'-dinonyl-2,2'-dipyridyl)$_2$][Pt(CN)$_4$] in toluene

For the production of OLEDs, a 2% by weight solution, for example, is prepared by dissolving 200 mg of [Pt(4,4'-dinonyl-2,2'-dipyridyl)$_2$][Pt(CN)$_4$] in 9.8 g of anisole.

Example 2

Preparation of [Pd(bpy)$_2$]$_{0.9}$[Pt(bpy)$_2$]$_{0.1}$[Pt(CN)$_4$]

A mixture of [Pd(2,2'-dipyridyl)$_2$][BF$_4$]$_2$ (533.1 mg, 0.9 mmol) and [Pt(2,2'-dipyridyl)$_2$][BF$_4$]$_2$ (68.1 mg, 0.1 mmol) is dissolved in 50 ml of dichloromethane. A solution of [n-Bu$_4$N]$_2$[Pt(CN)$_4$] (689.0 mg, 1.0 mmol) in 30 ml of dichloromethane is added to this solution with vigorous stirring, and the mixture is stirred at room temperature for a further 2 h. The solvent is removed in vacuo, the yellow solid is taken up in 50 ml of acetonitrile, the suspension is stirred at room temperature for 12 h and filtered with suction, and the process is repeated three times. After the final suction filtration, the product is washed five times with 20 ml of acetonitrile and subsequently dried in vacuo. Yield: 95%.

Dispersion of [Pd(bpy)$_2$]$_{0.9}$[Pt(bpy)$_2$]$_{0.1}$[Pt(CN)$_4$] in toluene A suspension of 200 mg of [Pd(bpy)$_2$]$_{0.9}$[Pt(bpy)$_2$]$_{0.1}$[Pt(CN)$_4$] in 9.8 g of toluene is treated with ultrasound for 15 h. The resultant dispersion is subsequently filtered.

The following compound is obtained analogously by using the suitable stoichiometry of the starting materials:

| Ex. No. | Compound | Yield |
|---|---|---|
| 3 | [Pd(bpy)$_2$]$_{0.99}$[Pt(bpy)$_2$]$_{0.01}$[Pt(CN)$_4$] | 95% |

Dispersion of [Pd(bpy)$_2$]$_{0.99}$[Pt(bpy)$_2$]$_{0.01}$[Pt(CN)$_4$] in toluene A suspension of 200 mg of [Pd(bpy)$_2$]$_{0.9}$[Pt(bpy)$_2$]$_{0.1}$[Pt(CN)$_4$] in 9.8 g of toluene is treated with ultrasound for 15 h. The resultant dispersion is subsequently filtered.

The following compounds were prepared by literature methods and employed as a 2% by weight dispersion in a mixture of toluene and DMF (1:1, v:v).

| Ex. No. | Compound | CAS No. |
| --- | --- | --- |
| 4 | [Pt(bpy)$_2$][Pt(CN)$_4$] | 54806-40-5 |
| 5 | [Pt(4,4'-di(Me)bpy)$_2$][Pt(CN)$_4$] | 138736-38-6 |
| 6 | [Pt(phen)$_2$][Pt(CN)$_4$] | 59981-69-0 |
| 7 | [Pt(phen)$_2$][Pt(Ox)$_4$] | 59981-70-3 |
| 8 | [Pt(bpy)$_2$][PtCl$_4$] | 54822-44-5 |
| 9 | [Pt(phen)(en)][Pt(CN)$_4$] | 136503-94-1 |

Example 10

Production and Characterisation of Organic Electroluminescent Devices from Solution LEDs are produced by the general process outlined below. This must of course be adapted in individual cases to the respective circumstances (for example layer-thickness variation in order to achieve optimum efficiency or colour).

General Process for the Production of OLEDs:

The production of such components is based on the production of polymeric light-emitting diodes (PLEDs), which has already been described many times in the literature (for example in WO 2004/037887 A2). In the present case, the following matrix materials or matrix-material combinations are dissolved in an organic solvent, such as, for example, toluene, chlorobenzene, anisole or DMF. The typical solids content of such solutions is between 10 and 25 g/l if, as here, the typical layer thickness of 80 nm for a device is to be achieved by means of spin coating.

Matrix Materials Used:

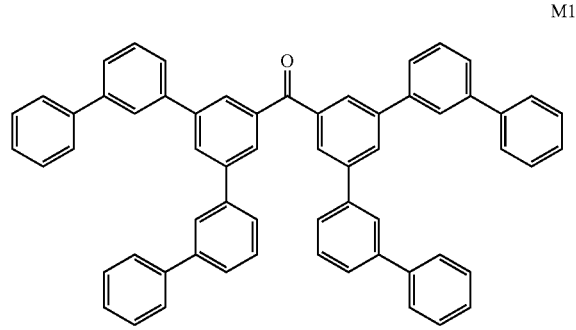

M1

DE 102008033943.1

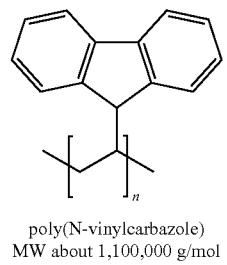

M2 poly(N-vinylcarbazole)
MW about 1,100,000 g/mol

A solution (see Ex. 1) or a nanodispersion (see Ex. 2-9) of the corresponding double-complex salt is then added to these solutions, where the ratio, based on the solids, of matrix material or matrix-material combination to double-complex salt is 5% by weight.

OLEDs having the following structure are produced analogously to the general process mentioned above:

PEDOT 20 nm (spin-coated from water; PEDOT purchased from BAYER AG; poly[3,4-ethylenedioxy-2,5-thiophene], Matrix+emitter 80 nm, 5% by weight of emitter+95% of matrix material or matrix-material combination, spin-coated from toluene, chlorobenzene or DMF, Ba/Ag 10 nm of Ba/150 nm of Ag as cathode.

Structured ITO substrates and the material for the so-called buffer layer (PEDOT, actually PEDOT:PSS) are commercially available (ITO from Technoprint and others, PEDOT:PSS as Clevios Baytron P aqueous dispersion from H. C. Starck). The emission layer is applied by spin coating in an inert-gas atmosphere, in the present case argon, and dried by heating at 170° C. for 10 min. Finally, a cathode comprising barium and aluminium is applied by vacuum vapour deposition. The solution-processed devices are characterised by standard methods, the OLED examples mentioned have not yet been optimised.

Table 2 shows the efficiency and voltage at 100 cd/m$^2$ and the colour.

TABLE 2

| | Device results | | |
| --- | --- | --- | --- |
| Ex. | Matrices, M Emitter, E | EQE at 100 cd/m$^2$, [%] | Voltage at 100 cd/m$^2$, [V] | CIE x/y |
| 11 | M1, 30% by wt. M2, 65% by wt. E1, 5% by wt. | 14.3 | 6.2 | 0.55/0.38 |
| 12 | M2, 95% by wt. E1, 5% by wt. | 16.3 | 5.9 | 0.53/0.39 |
| 13 | M1, 30% by wt. M2, 65% by wt. E2, 5% by wt. | 9.3 | 7.8 | 0.25/0.37 |
| 14 | M1, 30% by wt. M2, 65% by wt. E3, 5% by wt. | 8.7 | 7.5 | 0.21/0.29 |
| 15 | M1, 50% by wt. M2, 45% by wt. E6, 5% by wt. | 1.3 | 6.3 | 0.70/0.29 |
| 16 | M1, 50% by wt. M2, 45% by wt. E9, 5% by wt. | 17.3 | 5.6 | 0.36/0.59 |

The invention claimed is:
1. An organic electroluminescent device comprising an oligomer
wherein the oligomer is
a double-complex salt comprising at least one positively charged metal complex $K_1$ and at least one negatively charged metal complex $K_2$,
where $K_1$ has one of the following formulae (85), (86), (87), (90), (94), (122), (130), (132), (134), (136):
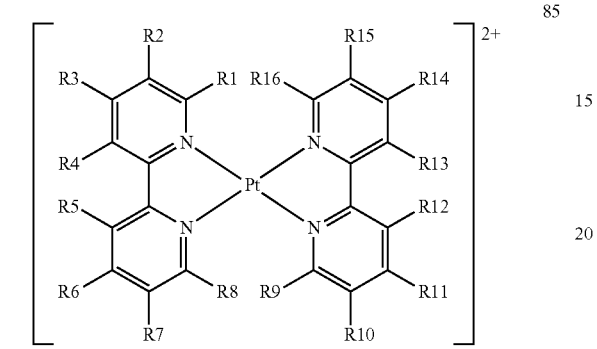
85
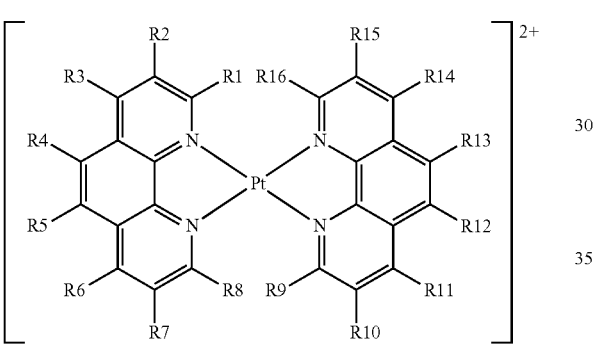
86
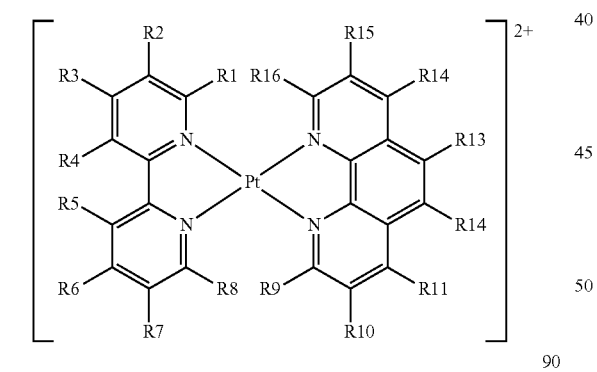
87
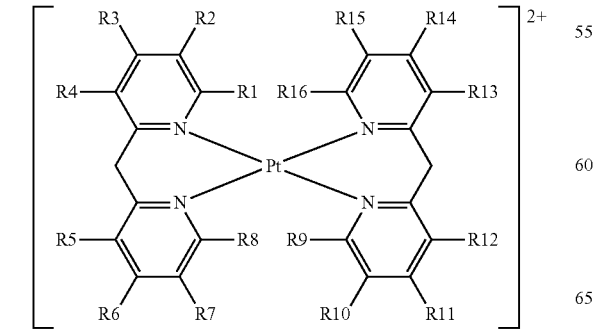
90
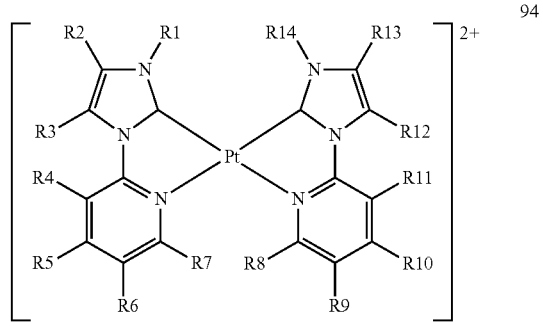
94
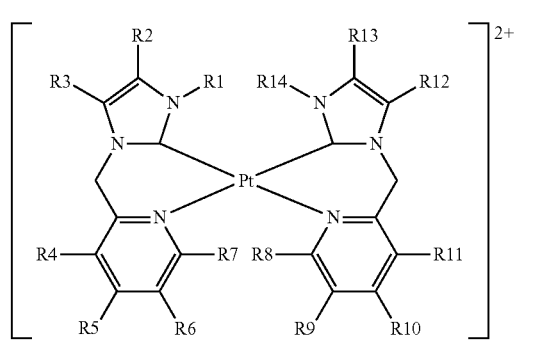
122
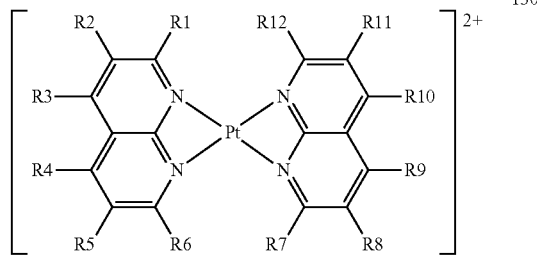
130
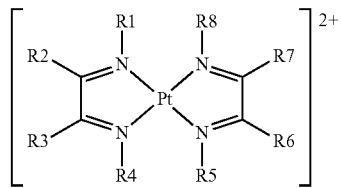
132
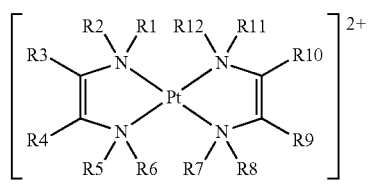
134
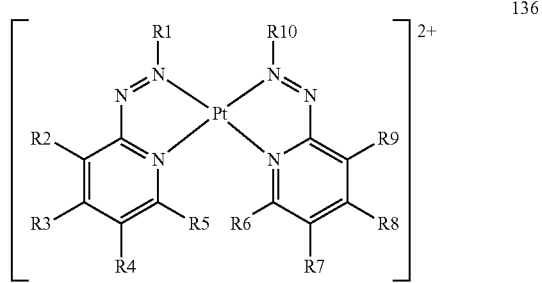
136
and

$K_2$ is selected from formula (158)

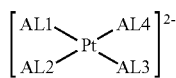

where
R1 to R16 are, identically or differently on each occurrence, one of the following groups: H, deuterium, F, Cl, Br, I, $N(R^{21})_2$, CN, $NO_2$, $Si(R^{21})_3$, $B(OR^{21})_2$, $C(=O)R^{21}$, $P(=O)(R^{21})_2$, $S(=O)R^{21}$, $S(=O)_2R^{21}$, $OSO_2R^{21}$, a straight chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^{21}$, where one or more adjacent $CH_2$ groups may be replaced by $R^{21}C=CR^{21}$, $C≡C$, $Si(R^{21})_2$, $Ge(R^{21})_2$, $Sn(R^{21})_2$, $C=O$, $C=S$, $C=Se$, $C=NR^{21}$, $P(=O)(R^{21})$, SO, $SO_2$, $NR^{21}$, O, S or $CONR^{21}$ and where one or more H atoms may be replaced by F, Cl, Br, I, CN or $NO_2$, or an aromatic or heteroaromatic ring system having 5 to 60 aromatic ring atoms, which may in each case be substituted by one or more radicals $R^{21}$, or an aryloxy or heteroaryloxy group having 5 to 60 aromatic ring atoms, which may be substituted by one or more radicals $R^{21}$, or a diarylamino group, diheteroarylamino group or arylheteroarylamino group having 10 to 40 aromatic ring atoms, which may be substituted by one or more radicals $R^{21}$, or a combination of these systems; two or more of these substituents may also form a mono- or polycyclic, aliphatic, aromatic and/or benzo-fused ring system with one another;

$R^{21}$ is on each occurrence, identically or differently, H, F or an aliphatic, aromatic and/or heteroaromatic radical having 1 to 20 C atoms, in which, in addition, one or more H atoms may be replaced by F; two or more substituents $R^{21}$ here may also form a mono- or polycyclic, aliphatic or aromatic ring system with one another;

AL1, AL2, AL3, AL4 are each, identically or differently on each occurrence, an anionic ligand selected from hydride, deuteride, the halides F, Cl, Br and I, alkylacetylides, arylacetylides, aryl groups, alkyl groups, alkenyl groups, borates, cyanide, cyanate, isocyanate, thiocyanate, isothiocyanate, aliphatic or aromatic alcoholates, aliphatic or aromatic thioalcoholates, amides, carboxylates and anionic, nitrogen-containing heterocycles;

wherein the device is hermetically screened from the environment.

2. Process for the production of an organic electroluminescent device according to claim 1, comprising applying the at least one positively charged metal complex $K_1$ and the at least one negatively charged metal complex $K_2$ in the form of a dispersion or where components of the at least one positively charged metal complex $K_1$ are introduced in the form of a solution and components of the at least one negatively charged metal complex $K_2$ are introduced by diffusion.

3. An organic electroluminescent device according to claim 1, wherein $K_2$ is selected from formula (138), (139), (140) and (141)

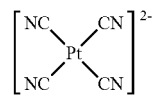

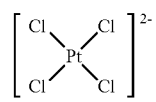

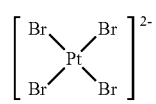

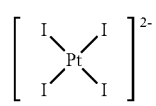

* * * * *